US011139065B1

(12) United States Patent
Gottman et al.

(10) Patent No.: US 11,139,065 B1
(45) Date of Patent: Oct. 5, 2021

(54) RELATIONSHIP-ANALYSIS SYSTEM THAT GENERATES A TRUST METRIC

(71) Applicant: Affective Software, Inc., Seattle, WA (US)

(72) Inventors: John Gottman, Deer Harbor, WA (US); Vladimir Brayman, Mercer Island, WA (US); Rafael Lisitsa, Seattle, WA (US)

(73) Assignee: Affective Software, Inc., Seattle, WA (US)

( * ) Notice: Subject to any disclaimer, the term of this patent is extended or adjusted under 35 U.S.C. 154(b) by 0 days.

(21) Appl. No.: 16/869,251

(22) Filed: May 7, 2020

Related U.S. Application Data

(63) Continuation-in-part of application No. 16/175,547, filed on Oct. 30, 2018.

(60) Provisional application No. 62/578,645, filed on Oct. 30, 2017.

(51) Int. Cl.
*G16H 80/00* (2018.01)
*G16H 20/70* (2018.01)
*G06F 17/16* (2006.01)
*G16H 40/67* (2018.01)

(52) U.S. Cl.
CPC ............ *G16H 20/70* (2018.01); *G06F 17/16* (2013.01); *G16H 40/67* (2018.01); *G16H 80/00* (2018.01)

(58) Field of Classification Search
USPC ................................................ 348/14, 10
See application file for complete search history.

(56) References Cited

U.S. PATENT DOCUMENTS

| | | | | |
|---|---|---|---|---|
| 2011/0219073 | A1* | 9/2011 | Lawler | G06F 15/16 709/204 |
| 2016/0078358 | A1* | 3/2016 | Baveja | G06N 5/048 706/52 |
| 2017/0054611 | A1* | 2/2017 | Tiell | H04L 43/0876 |

* cited by examiner

*Primary Examiner* — Amal S Zenati
(74) *Attorney, Agent, or Firm* — Olympic Patent Works pLLC

(57) ABSTRACT

The current document is directed to a relationship-analysis system. The currently disclosed relationship-analysis system collects objective and subjective observations of participants, and their relationship, in an interaction or transaction. The objective and subjective observations are combined to generate an observation data set that is processed by a computational relationship-analysis system. The analysis produces a variety of different types of results, including trust metrics, and stores the results in memory and/or mass-storage for control of downstream analysis, reporting, and actions. Trust metrics provide a basis for carrying out numerous types of downstream actions and for generating recommendations and evaluations by various types of relationship-evaluation and relationship-management systems that employ the relationship-analysis system.

2 Claims, 38 Drawing Sheets

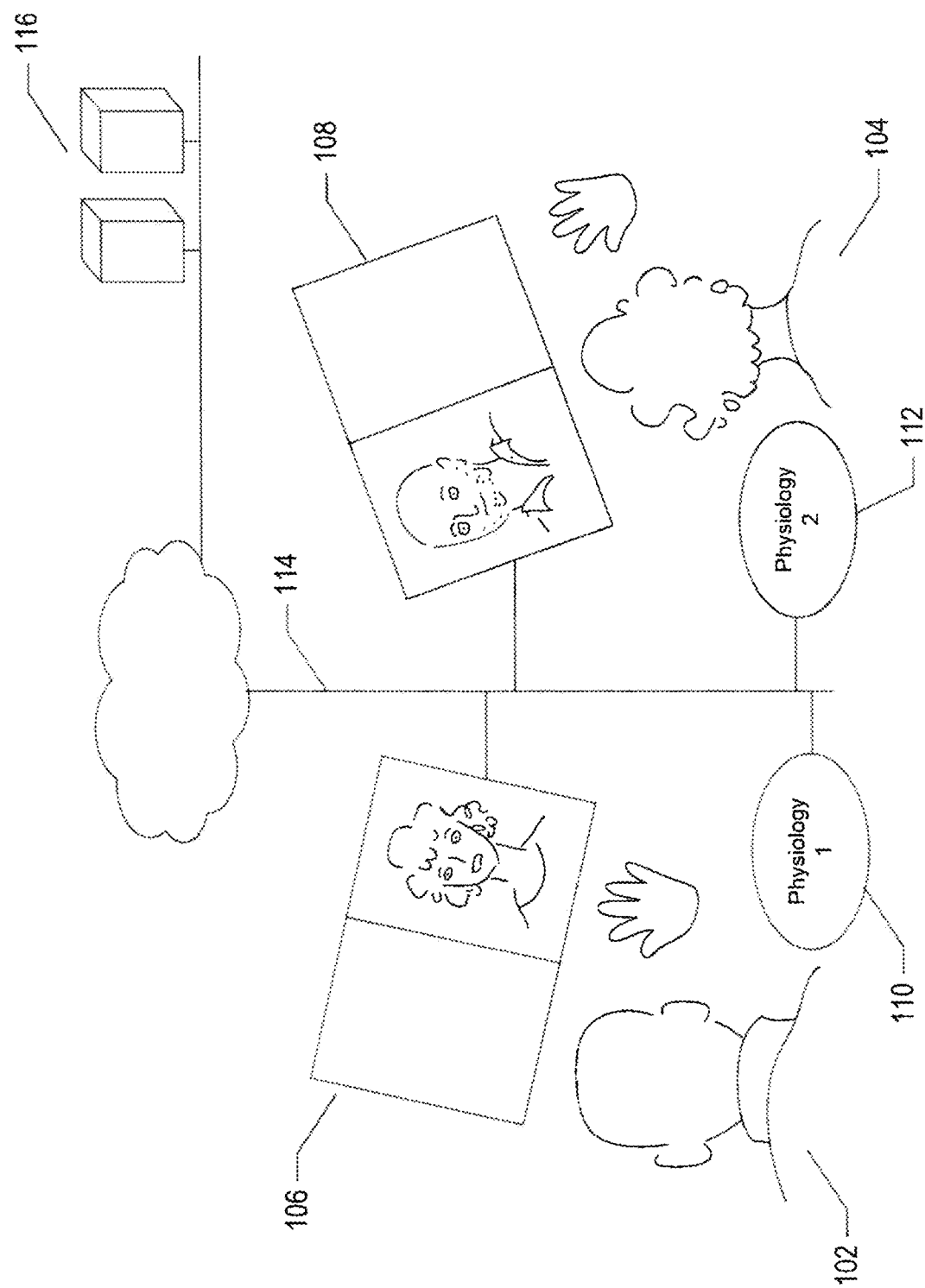

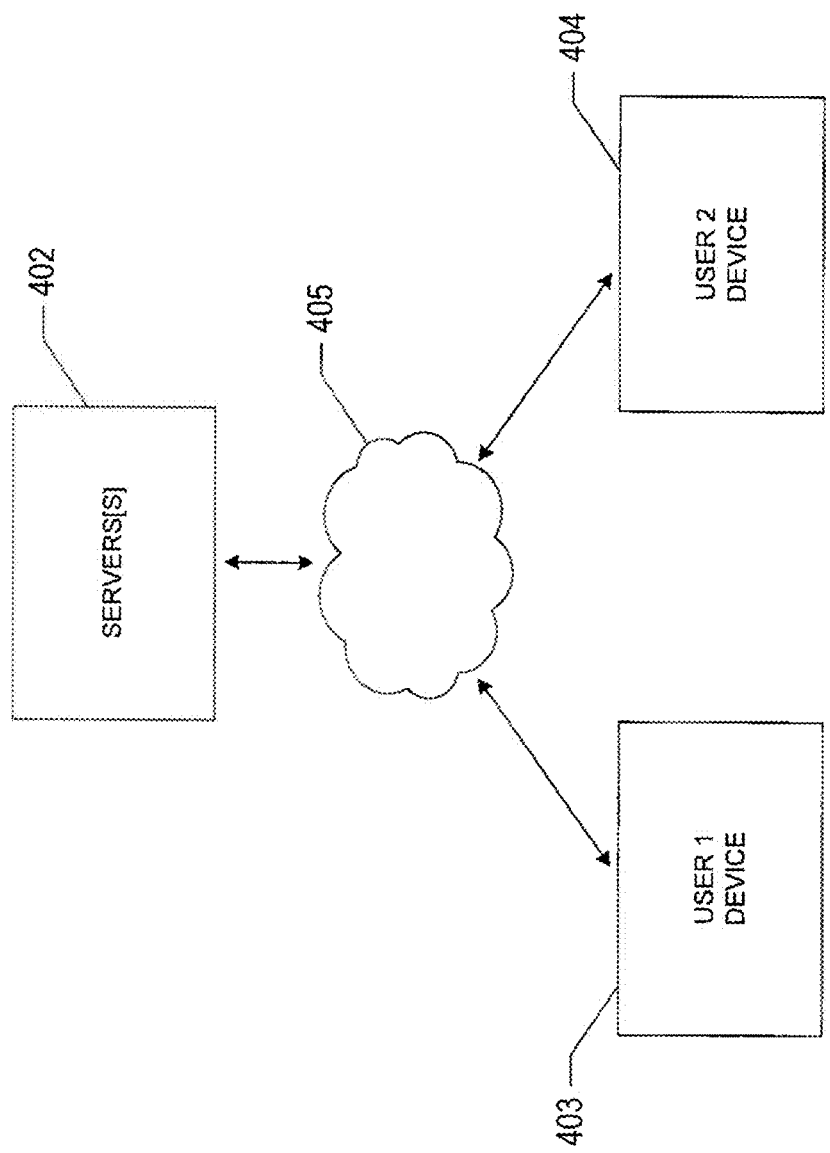

| t | dial |
|---|------|
| 0 | 6.0 |
| 1 | 6.1 |
| 2 | 5.5 |
| 3 | 3.4 |
| 4 | 4.1 |
| 5 | 7.7 |
| 6 | 8.1 |
| 7 | 5.5 |
| 8 | 4.0 |
| 9 | 3.1 |
| 10 | 6.7 |
| 11 | 6.1 |
| 12 | 9.6 |
| 13 | 5.8 |
| 14 | 6.0 |
| 15 | 4.0 |
| ... | ... |
| 1198 | 7.7 |
| 1199 | 7.2 |

(1006 brace indicating rows near end)

S/P1 (1003)

| t | dial |
|---|------|
| 0 | 4.2 |
| 1 | 4.6 |
| 2 | 4.1 |
| 3 | 3.0 |
| 4 | 3.7 |
| 5 | 4.6 |
| 6 | 4.9 |
| 7 | 7.2 |
| 8 | 6.8 |
| 9 | 6.1 |
| 10 | 5.5 |
| 11 | 5.1 |
| 12 | 5.8 |
| 13 | 6.1 |
| 14 | 5.7 |
| 15 | 4.1 |
| ... | ... |
| 1198 | 6.1 |
| 1199 | 5.7 |

O/P0 (1004)

| t | dial |
|---|------|
| 0 | 0 |
| 1 | 0 |
| 2 | 0 |
| 3 | -1 |
| 4 | -1 |
| 5 | 0 |
| 6 | -1 |
| 7 | 1 |
| 8 | 1 |
| 9 | 1 |
| 10 | -1 |
| 11 | 0 |
| 12 | 1 |
| 13 | 1 |
| 14 | 0 |
| 15 | 0 |
| ... | ... |
| 1198 | 0 |
| 1199 | 0 |

O/P1 (1005)

| t | dial |
|---|------|
| 0 | 0 |
| 1 | 0 |
| 2 | 1 |
| 3 | -1 |
| 4 | -1 |
| 5 | -1 |
| 6 | -1 |
| 7 | 1 |
| 8 | 1 |
| 9 | 1 |
| 10 | 1 |
| 11 | 0 |
| 12 | 0 |
| 13 | 0 |
| 14 | 0 |
| 15 | 0 |
| ... | ... |
| 1198 | -1 |
| 1199 | 0 |

FIG. 12

Table 1202 (left):

| context | $P_0$ | $P_1$ |
|---|---|---|
| (0,0) | 6.0 | 3.0 |
|  | 6.1 | 3.4 |
| (0,-1) | 5.5 | 3.1 |
| (-1,-1) | 3.4 | 1.9 |
|  | 4.1 | 2.7 |
| (0,-1) | 7.7 | 3.4 |
| (1,-1) | 8.1 | 4.9 |
| (1,1) | 5.5 | 7.0 |
|  | 4.0 | 6.8 |
| (-1,1) | 3.1 | 6.0 |
| (0,1) | 6.7 | 5.4 |
| (0,0) | 6.1 | 5.0 |
| (1,0) | 9.6 | 5.7 |
|  | 5.8 | 6.0 |
| (0,0) | 8.0 | 5.6 |
|  | 4.0 | 3.1 |
| (0,1) | 3.6 | 2.7 |
| (0,-1) | 4.1 | 1.1 |
|  | 5.1 | 2.5 |
|  | 5.8 | 3.8 |
| (0,0) | 5.7 | 5.0 |
| (-1,0) | 3.1 | 6.0 |
|  | 7.0 | 7.0 |
|  | 5.1 | 6.6 |
|  | 4.5 | 7.0 |
|  | 3.0 | 4.1 |
| (1,0) | 8.1 | 5.0 |
|  | 7.7 | 5.7 |
|  | 7.1 | 5.9 |
| (0,0) | 6.2 | 6.6 |
| (0,1) | 5.7 | 6.0 |
| (0,-1) | 5.2 | 3.0 |
|  | 4.9 | 4.1 |
| (1,-1) | 8.0 | 4.8 |
| (1,0) | 4.1 | 5.0 |
| (0,0) | 4.7 | 5.5 |
| (0,1) | 4.2 | 6.0 |
|  | 2.1 | 2.0 |
| (0,0) | 4.3 | 2.7 |
| (0,-1) | 4.8 | 3.0 |
|  | 5.0 | 2.7 |
|  | 7.1 | 3.0 |
| (-1,-1) | 5.7 | 3.8 |
| (-1,-1) | 6.0 | 7.1 |
| (0,1) | 9.0 | 6.7 |
| (0,0) | 7.0 | 5.8 |
| (-1,0) | 6.5 | 5.1 |
|  | 3.1 | 5.7 |
|  | 5.0 | 6.0 |
|  | 5.3 | 6.6 |
| (0,1) | 6.0 | 7.0 |

Table 1214 (right):

| context | $P_0$ | $P_1$ |
|---|---|---|
| (-1,-1) | 3.4 | 1.9 |
|  | 4.1 | 2.7 |
|  | 5.7 | 3.8 |
| (0,-1) | 5.5 | 3.1 |
|  | 7.7 | 3.4 |
|  | 4.1 | 1.1 |
|  | 5.1 | 2.5 |
|  | 5.8 | 3.8 |
|  | 5.2 | 3.0 |
|  | 4.9 | 4.1 |
|  | 4.8 | 3.0 |
|  | 5.0 | 2.7 |
|  | 7.1 | 3.0 |
| (1,-1) | 8.1 | 4.9 |
|  | 8.0 | 4.8 |
| (-1,0) | 3.1 | 6.0 |
|  | 7.0 | 7.0 |
|  | 5.1 | 6.6 |
|  | 4.5 | 7.0 |
|  | 3.0 | 4.1 |
|  | 6.5 | 5.1 |
|  | 3.1 | 5.7 |
|  | 5.0 | 6.0 |
|  | 5.3 | 6.6 |
| (0,0) | 6.0 | 3.0 |
|  | 6.1 | 3.4 |
|  | 6.1 | 5.0 |
|  | 6.0 | 5.6 |
|  | 4.0 | 3.1 |
|  | 5.7 | 5.0 |
|  | 6.2 | 6.6 |
|  | 4.7 | 5.5 |
|  | 4.3 | 2.7 |
|  | 7.0 | 5.8 |
| (1,0) | 9.6 | 5.7 |
|  | 5.8 | 6.0 |
|  | 8.1 | 5.0 |
|  | 7.7 | 5.7 |
|  | 7.1 | 5.9 |
|  | 4.1 | 5.0 |
| (-1,1) | 3.1 | 6.0 |
|  | 6.0 | 7.1 |
| (0,1) | 6.7 | 5.4 |
|  | 3.6 | 2.7 |
|  | 5.7 | 6.0 |
|  | 4.2 | 6.0 |
|  | 2.1 | 2.0 |
|  | 9.0 | 6.7 |
|  | 6.0 | 7.0 |
| (1,1) | 5.5 | 7.0 |
|  | 4.0 | 6.8 |

$$D_x(P\_D_{\daleth x}, B\_D_x) = \frac{1}{2}[(\sum_i P\_D_{\daleth x}[i]\log_2\frac{P\_D_{\daleth x}[i]}{B\_D_x[i]}) + (\sum_i B\_D_x[i]\log_2\frac{B\_D_x[i]}{P\_D_{\daleth x}[i]}))]$$

where $x \in \{0, 1\}$, $\daleth 0 = 1$, $\daleth 1 = 0$,

P_D = preference distribution, and

B_D = behavior distribution $TM_x = \max(1-D_x, 0)$ where $TM_x$ = the level of trust that participant $\daleth x$ has for participant $x$

FIG. 17

$X = 0$
$P\_D_1 = (.34, .28, .38)$
$B\_D_0 = (.27, .53, .20)$
$D_0 = \frac{1}{2}[(.34\log_2\frac{.34}{.27} + .28\log_2\frac{.28}{.53} + .38\log_2\frac{.20}{.38}) +$
$\qquad (.27\log_2\frac{.27}{.34} + .53\log_2\frac{.53}{.28} + .20\log_2\frac{.38}{.20})]$
$\quad = \frac{1}{2}[.34(.333) + .28(-.921) + .38(-.926) +$
$\qquad .27(-.333) + .53(.921) + .20(.926)]$
$\quad = \frac{1}{2}[-.498 + .583]$
$\quad = .0854$
$TM_0 = 0.915$ ⎫ 1802

$X = 1$
$P\_D_0 = (.36, .35, .29)$
$B\_D_1 = (.29, .49, .22)$
$D_1 = \frac{1}{2}[(.36\log_2\frac{.36}{.29} + .35\log_2\frac{.35}{.49} + .29\log_2\frac{.29}{.22}) +$
$\qquad (.29\log_2\frac{.29}{.36} + .49\log_2\frac{.49}{.35} + .22\log_2\frac{.22}{.29})]$
$\quad = \frac{1}{2}[.36(.312) + .35(-.485) + .29(.399) +$
$\qquad .29(-.312) + .49(.485) + .22(-.399)]$
$\quad = \frac{1}{2}[.058 + .059]$
$\quad = .059$
$TM_1 = 0.942$ ⎫ 1804

$X = 0$
$P\_D_1 = (.01, .04, .95)$
$B\_D_0 = (.96, .03, .01)$
$D_0 = \frac{1}{2}[.01\log_2\frac{.01}{.96} + .04\log_2\frac{.04}{.03} + .95\log_2\frac{.95}{.01} + .96\log_2\frac{.96}{.01} + .03\log_2\frac{.03}{.04} + .01\log_2\frac{.01}{.96}]$
$\quad = \frac{1}{2}[.01(-6.58) + .04(.415) + .95(6.57) + .96(6.58) + .03(-.415) + .01(-6.57)]$
$\quad = 6.22$
$TM_0 = 0$ ⎫ 1806

$X = 1$
$P\_D_0 = (.01, .04, .95)$
$B\_D_1 = (.01, .03, .96)$
$D_1 = \frac{1}{2}[.01\log_2\frac{.01}{.01} + .04\log_2\frac{.04}{.03} + .95\log_2\frac{.95}{.96} + .01\log_2\frac{.01}{.01} + .03\log_2\frac{.03}{.04} + .96\log_2\frac{.96}{.95}]$
$\quad = \frac{1}{2}[.01(0) + .04(.415) + .95(-.0151) + .01(0) + .03(-.415) + .96(.0151)]$
$\quad = .0022$
$TM_1 = .998$ ⎫ 1808

FIG. 18A

X = 0
P_D$_1$ = (.20, .30, .40)
B_D$_0$ = (.45, .25, .30)
D$_0$ = $\frac{1}{2}$[.20log$_2$$\frac{.20}{.45}$ + .30log$_2$$\frac{.30}{.25}$ + .40log$_2$$\frac{.40}{.30}$ + .45log$_2$$\frac{.45}{.20}$ + .25log$_2$$\frac{.25}{.30}$ + .30log$_2$$\frac{.30}{.40}$]
  = $\frac{1}{2}$[.20(-1.17) + .30(.263) + .40(.415) + .45(1.17) + .25(-.263) + .30(-.415)]
  = .176
TM$_0$ = .824

---

X = 1
P_D$_0$ = (.10, .20, .70)
B_D$_1$ = (.40, .30, .30)
D$_1$ = $\frac{1}{2}$[.10log$_2$$\frac{.10}{.40}$ + .20log$_2$$\frac{.20}{.30}$ + .70log$_2$$\frac{.70}{.30}$ + .40log$_2$$\frac{.40}{.10}$ + .30log$_2$$\frac{.30}{.20}$ + .30log$_2$$\frac{.30}{.70}$]
  = $\frac{1}{2}$[.10(-2.0) + .20(-.585) + .70(1.22) + .40(2.0) + .30(.585) + .30(-1.22)]
  = .573
TM$_0$ = .427

FIG. 18B

RELATIONSHIP-ANALYSIS SYSTEM THAT GENERATES A TRUST METRIC

CROSS-REFERENCE TO RELATED APPLICATIONS

This application is a continuation-in-part of application Ser. No. 16/175,547, filed Oct. 30, 2018, which claims the benefit of Provisional Application No. 62/578,645, filed Oct. 30, 2017.

TECHNICAL FIELD

The current document is directed to distributed computer systems and automated analysis systems, and, in particular, to a relationship-analysis system that generates a trust metric.

BACKGROUND

Computer systems and computational technologies have steadily evolved, during the past 70 years, from initial vacuum-tube-based systems that lacked operating systems, compilers, network connectivity, and most other common features of modern computing systems to vast distributed computing systems that include large numbers of multi-processor servers, data-storage appliances, and multiple layers of internal communications networks interconnected by various types of wide-area networks and that provide computational resources to hundreds, thousands, tens of thousands, or more remote users. As operating systems and virtualization layers have been developed and refined, over the years, in parallel with the advancements in computer hardware and networking, the robust execution environments provided by distributed operating systems and virtualization layers now provide a foundation for development and evolution of many different types of distributed application programs, including distributed database-management systems, distributed client-server applications, and distributed web-based service-provision applications.

In a different evolutionary trend in computing and electronics, small portable computing devices, including laptops, tablets, and smart phones, have gained widespread acceptance and are increasingly replacing PCs and other desk top computers. Just as desktop computers overtook minicomputers in computational bandwidth and cost effectiveness, smart phones are now overtaking traditional PCs and desktop computer systems, not only with respect to computational bandwidth, but perhaps more importantly with respect to usability and to matching provided functionalities with user needs. Interestingly, the average current smart phone has far greater memory capacity and instruction-execution bandwidth than supercomputers of up to the early 1990s.

Various types of relationship counseling have been in practice for hundreds of years. With the development of psychology and interest in psychology and emotional health over the past 100 years, more systematic approaches to relationship counseling have arisen. During the past 30 years, along with the development of processor-controlled electronic systems, electronic communications, and audio and visual functionalities that can be relatively easily incorporated into processor-controlled systems, various types of specialized and generally human-supervised relationship-analysis support systems have been developed, along with interactive relationship-analysis environments, to evaluate and diagnose problems in relationships and assist relationship-analysis patients to take steps to improve their relationships and personal emotional health. However, the specialized and human-supervised relationship-analysis-support systems have limited availability, are cumbersome and expensive to manage and maintain, and fail to take advantage of the many developments in distributed-computer systems and electronic communications, evolution of personal computing devices, and the availability of powerful pattern-recognition computational technologies, including machine-learning systems and classifiers, neural networks, and other new computational technologies. In addition, new and increasingly sophisticated capabilities of computer systems have given rise to many new types of human-with-human, human-with-computer, and computer-with-computer interactions, which involve various types of relationships that are amenable to computational analysis. Thus, inevitably, computational relationship analysis is destined to play and increasingly vital role in understanding relationships and managing interactions and transactions.

SUMMARY

The current document is directed to a relationship-analysis system. The currently disclosed relationship-analysis system collects objective and subjective observations of participants, and their relationship, in an interaction or transaction. The objective and subjective observations are combined to generate an observation data set that is processed by a computational relationship-analysis system. The analysis produces a variety of different types of results, including trust metrics, and stores the results in memory and/or mass-storage for control of downstream analysis, reporting, and actions. Trust metrics provide a basis for carrying out numerous types of downstream actions and for generating recommendations and evaluations by various types of relationship-evaluation and relationship-management systems that employ the relationship-analysis system.

BRIEF DESCRIPTION OF THE DRAWINGS

FIGS. 1A-F illustrate an initial phase of a relationship-analysis session.

FIGS. 4A-C illustrate an architecture for one implementation of the semi-automated, distributed, interactive relationship-counseling system ("SDIRCS").

FIG. 10 illustrates an example observation data set collected from a relationship-analysis session by the SDIRCS discussed in the preceding subsections of this document.

FIGS. 1A-B show 2-dimensional plots of the four individual data sets shown in FIG. 10.

FIG. 12 shows two alternative tabular representations of an observation data set comprising the initial 15 time-point/data-value pairs of the four individual data sets shown in FIG. 10 and plotted in FIGS. 11A-B.

FIG. 17 illustrates the process by which a trust metric is generated from preference and behavior distributions.

FIGS. 18A-B illustrate trust metrics calculated for various example distributions.

DETAILED DESCRIPTION

The current document is directed to a relationship-analysis system. In a first subsection, below, an overview of one type of relationship-analysis session is provided. In a second subsection, an overview of one type of semi-automated, distributed, interactive relationship-analysis-system architecture is provided. A third subsection discusses the variety of different types of relationship-evaluation and relationship-management systems that employ relationship-analysis systems as subsystems. A fourth subsection provides an overview of computational systems. A fifth subsection discusses trust metrics and a process that computes trust metrics from an electronically collected and stored observation data set.

An Overview of the Phases of an Example Relationship-Analysis Session

The current document is directed to a relationship-analysis system that can have many different specific implementations for use by a variety of different types of relationship-evaluation and relationship-management systems. One example of the currently disclosed relationship-analysis system is a component of a distributed, semi-automated, interactive relationship-counseling system. The distributed, semi-automated, interactive relationship-counseling system and the specific relationship-analysis system incorporated within the distributed, semi-automated, interactive relationship-counseling system are discussed in this subsection of the current document. It is important to note, however, that the currently disclosed relationship-analysis system encompasses many different specific implementations.

Figure 1B:
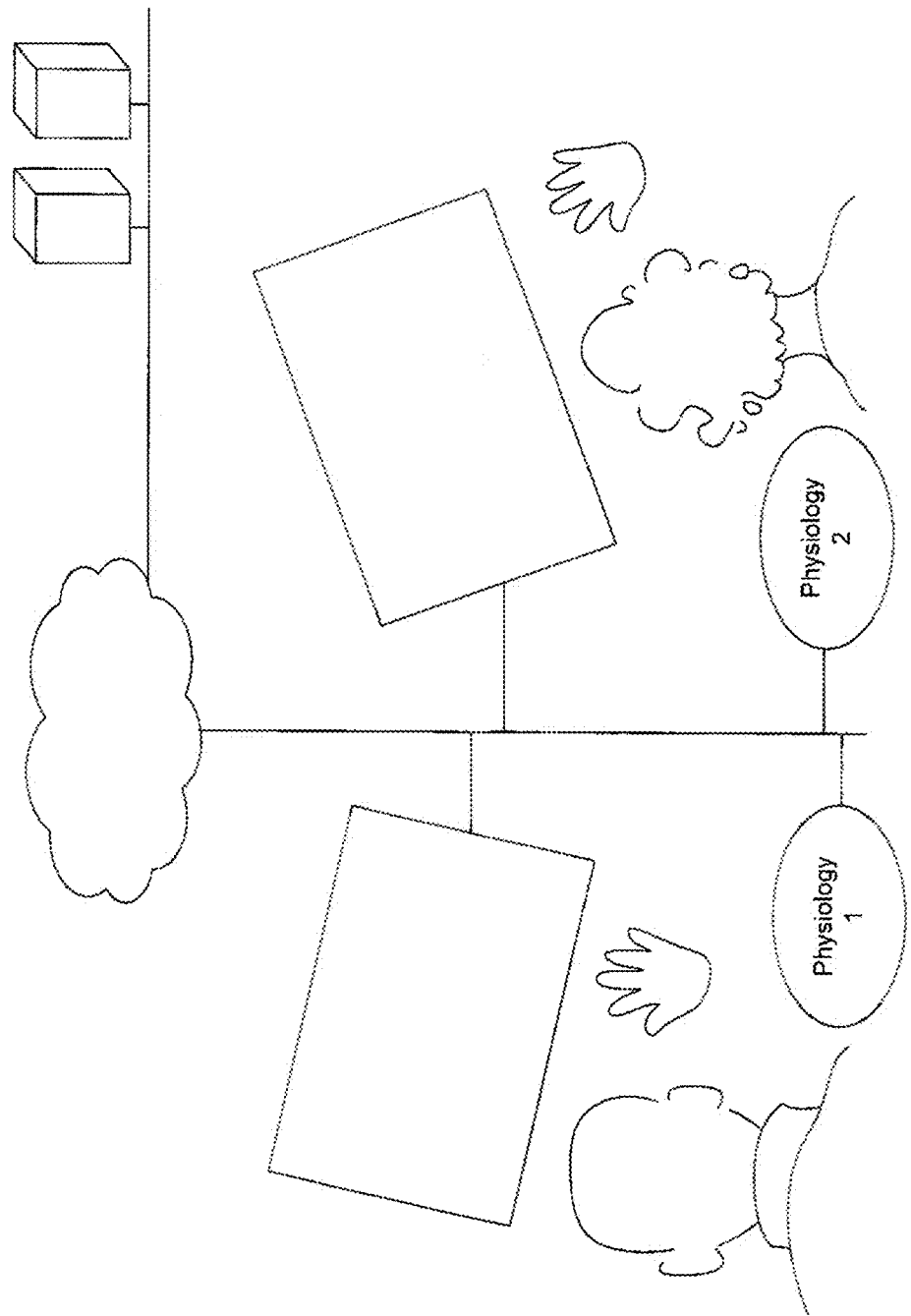

FIGS. 1A-F illustrate an initial phase of a relationship-analysis session carried out in a relationship-analysis environment provided by the currently disclosed semi-automated, distributed, interactive relationship-counseling system. FIG. 1A illustrates a relationship-analysis environment. As shown in FIG. 1A, the relationship-analysis environment includes a first participant 102 and a second participant 104. Each participant interacts with the participant's video-enabled electronic device 106 and 108 and may also be monitored by one or more physiological sensors 110 and 112. In certain cases, the physiological sensors may be in electronic communication with the video-enabled electronic devices while, in other cases, the physiological sensors may be directly or indirectly connected through electronic communications 114 to a remote relational-analysis-processing system 116. The two video-enabled electronic devices are also interconnected with the remote relational-analysis-processing system. During an initial phase of a relationship-analysis session, each participant can view the other participant on the video-enabled electronic device during a first-phase discussion. In many implementations, the device provides a split video screen allowing the participant to also view himself or herself during the first-phase discussion. In certain implementations, the participants share a single video-enabled electronic device.

Figure 1C:
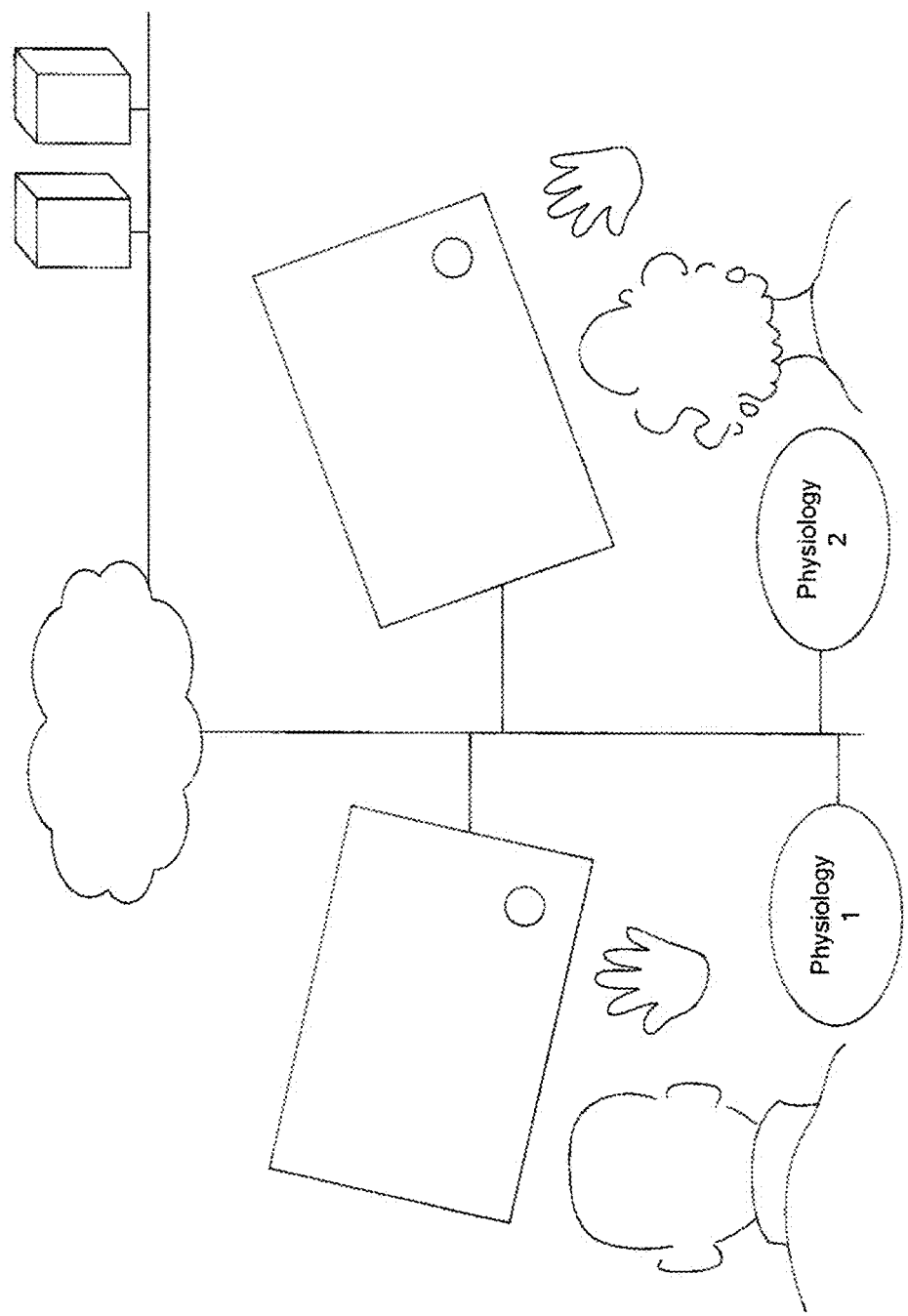
Figure 1D:
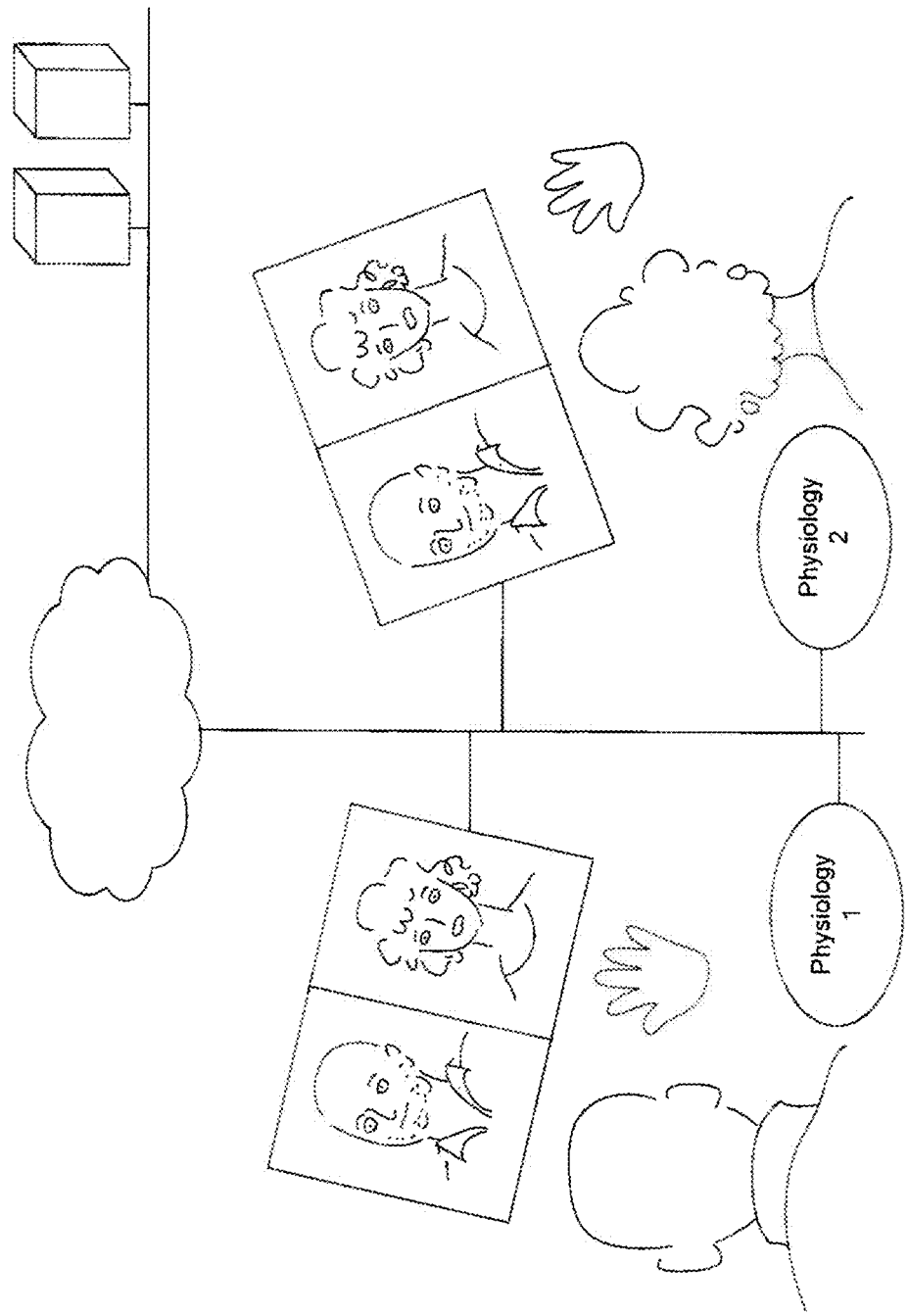
Figure 1E:
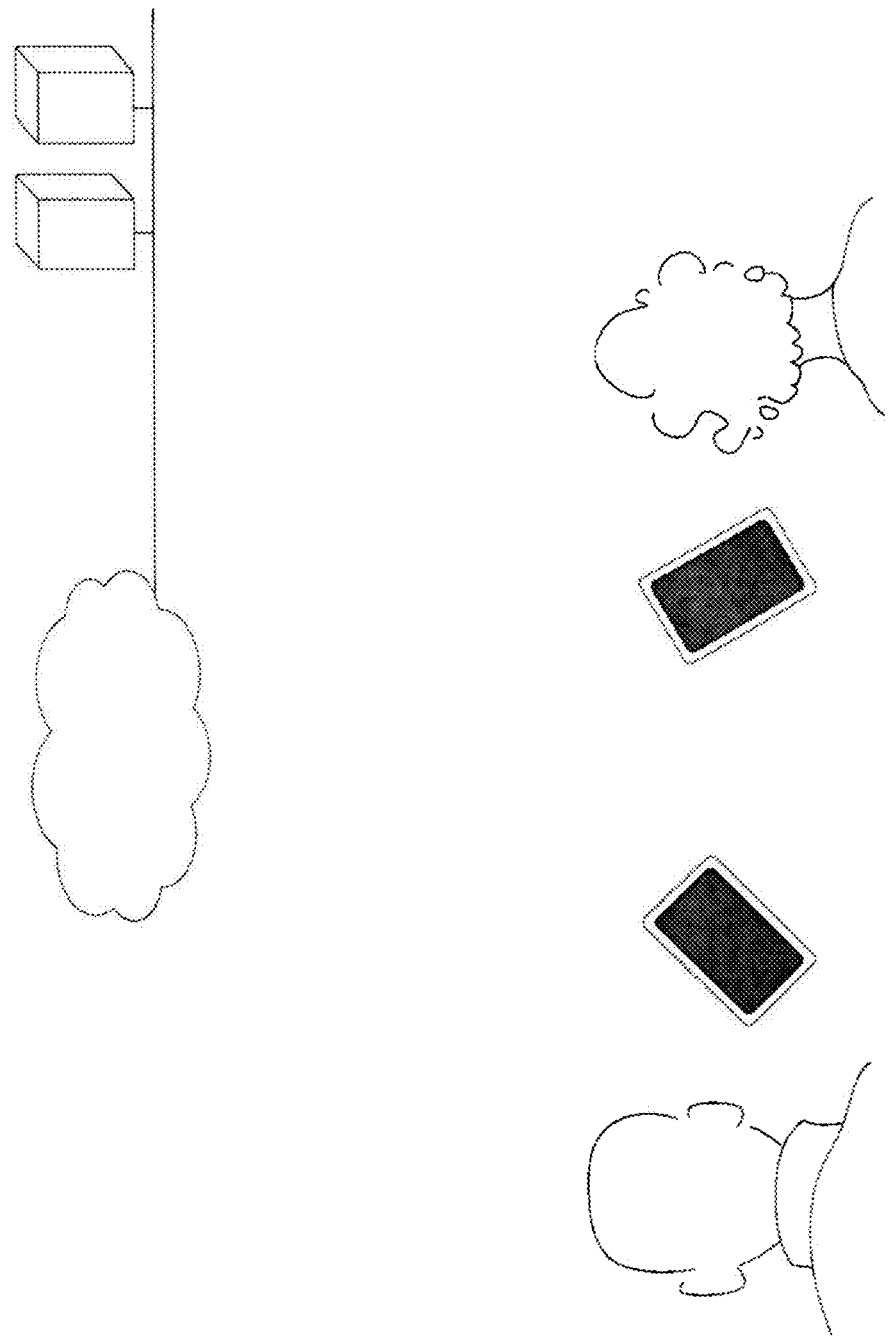

FIG. 1B shows the relationship-analysis environment prior to start of the initial phase of the relationship-analysis session. As shown in FIG. 1C, the participants power up their video-enabled electronic devices and launch a relationship-analysis application, in certain implementations, or, in other implementations, access relationship-analysis services through a web browser from a relationship-analysis-services web server within the relational-analysis-processing system. The relationship-analysis-services web server may be the same server that runs a relationship-analysis subsystem and other subsystems that together comprise the relational-analysis-processing system, may be another server in the same cloud-computing facility as the analysis-subsystem server, or may be geographically separate from the relational-analysis-processing system. Following user input to the relationship-analysis application or relationship-analysis services, a first-phase discussion is configured on behalf of the participants, their video-enabled electronic devices and physiological sensors may be prepared and for the first-phase discussion and tested, and a start feature 120 and 122 is displayed to each of the participants on the participants' video-enabled electronic devices. When the participants input an indication to the start features, the first-phase discussion begins, as shown in FIG. 1D. The participants' video-enabled electronic devices are in communication with a relationship-analysis-session-controller subsystem, in certain implementations, that may run on the same server as, or a different server than, the server that runs the relationship-analysis services and the server that includes the analysis subsystem. In other implementations, a distributed control function is implemented by the relationship-analysis applications running on the two video-enabled electronic devices or by the web server that provides relationship-analysis services. Initially, the participants may be provided with instructions for the first-phase discussion, including a topic or topics to be discussed and a set of ground rules, by the relationship-analysis-session controller. In certain implementations, participants may receive visual, graphical cues, or other information during the first-phase discussion in order to facilitate a desired level of interaction and a desired density of information collection. As shown in FIG. 1D, each participant can see both himself or herself as well as the other participant on his or her video-enabled electronic device. Following a fixed length of time for the first-phase discussion, or following determination that the first-phase discussion has reached an endpoint by the relationship-analysis-session controller, the first-phase discussion terminates and execution of the relationship-analysis application or connection to the relationship-analysis services provided by the web server also terminates, as shown in FIG. 1E. At this point in time, the collected information has been transferred, along with timing information, to the remote relational-analysis processing system.

During the first-phase discussion, a significant amount of data from audio and video inputs as well as from physiological sensors is collected. One purpose of the initial phase is to carefully record both participants during a discussion in order to calibrate the participants' voices, facial-expressions, and other characteristics, observe how the participants emotionally react to one another, perceive one another's statements, observations, facial expressions, gestures, posture, and other observable characteristics, and respond to one another's statements, observations, and perceived characteristics. The dynamics of the interaction, patterns observed in the interaction dynamics, and many other features of the recorded discussions may be analyzed by pattern-recognition and machine-learning subsystems within the relationship-analysis-processing system. These types of automated observations may contribute higher-level data to the subsequent relationship analysis. In addition, the recorded first-phase discussion is played back to the participants, individually, during a second phase of a relationship-analysis session during which participants provide a rating input as the first-phase discussion is played back.

Figure 1F:
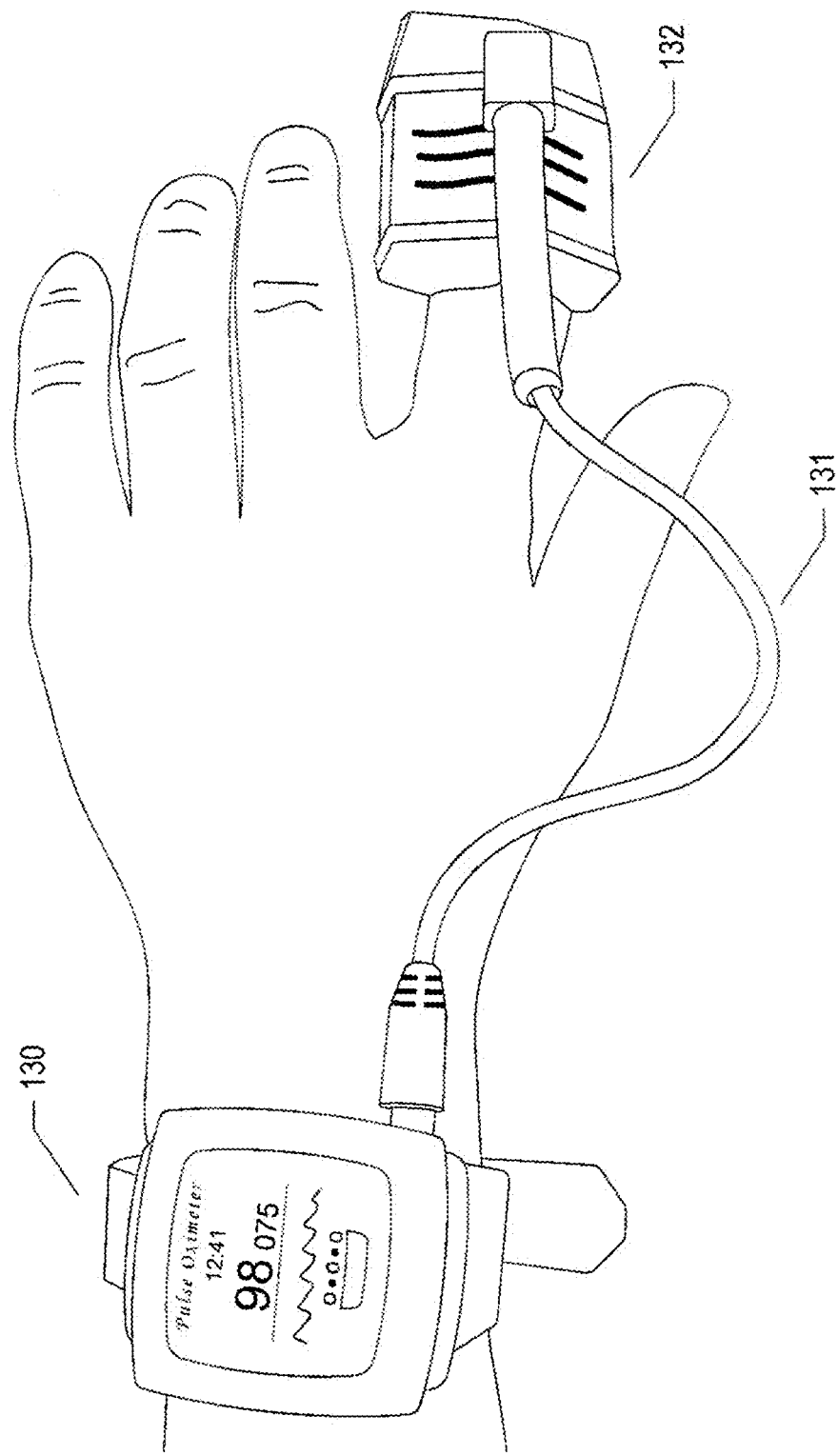

FIG. 1F shows one type of physiological sensor. The sensor 130-132 shown in FIG. 1F is a pulse oximeter, which continuously measures the level of oxygenation within a participant's blood as well as the pulse rate of the participant's heart. Many other types of physiological sensors may be employed in alternative implementations.

Figure 2A:
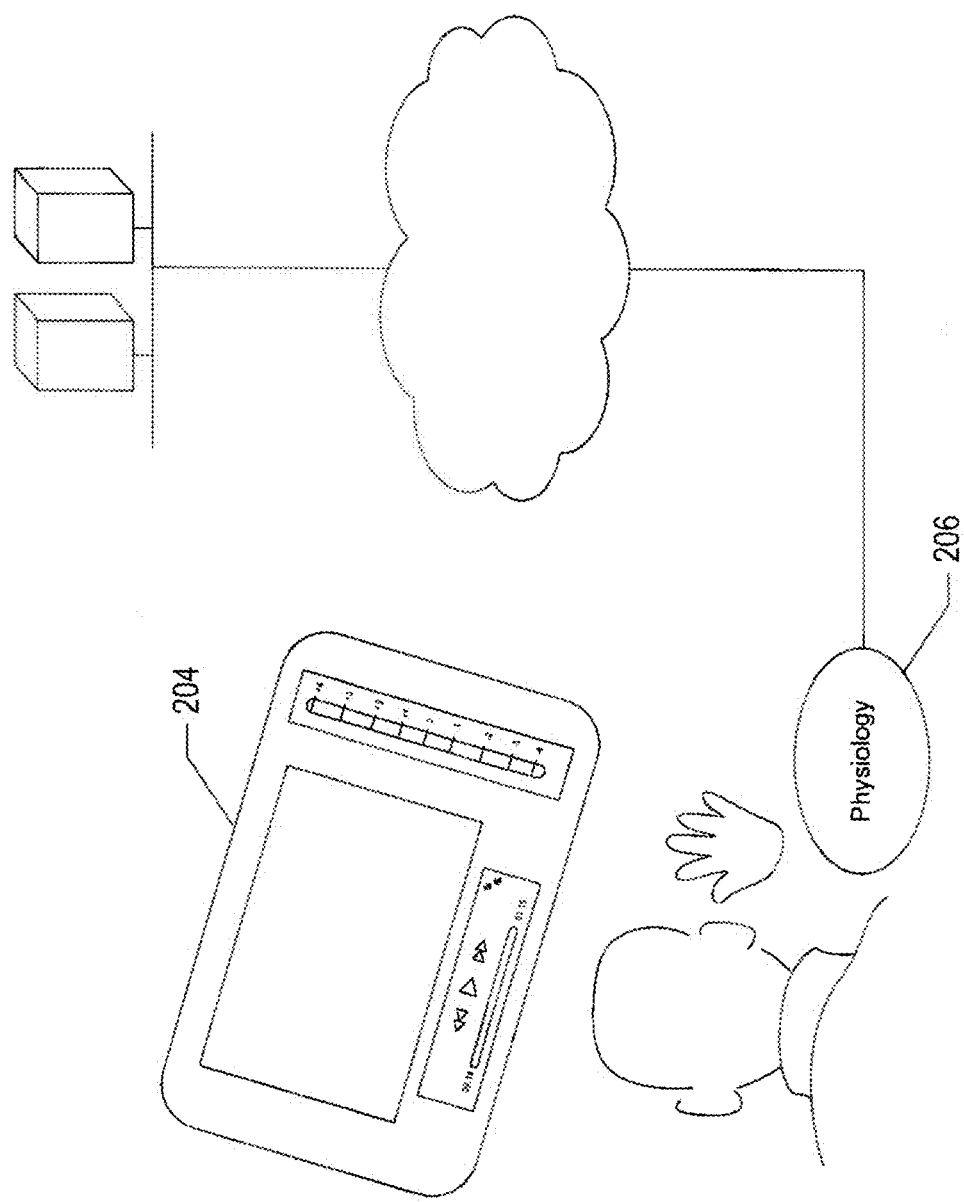
FIGS. 2A-D illustrate the second phase of a relationship-analysis session.

FIGS. 2A-E illustrate the second phase of a relationship-analysis session. In this second phase, also referred to below as a second-phase annotation sub-session, each of the two participants separately annotates the first-phase discussion previously recorded during the initial phase of the relationship-analysis session. As shown in FIG. 2A, during the second phase of the relationship-analysis session, the analysis environment includes a participant 202, the participant's video-enabled electronic device 204, and, in certain cases, one or more physiology sensors 206. The participant again powers on the video-enabled electronic device and launches a relationship-analysis application or connects to relationship-analysis services through a web browser. After providing inputs to solicit a second-phase annotation sub-session, a relationship-analysis-session-controller subsystem launches an annotation-session interactive display on the participants video-enabled electronic device and starts the second-phase annotation sub-session.

Figure 2B:
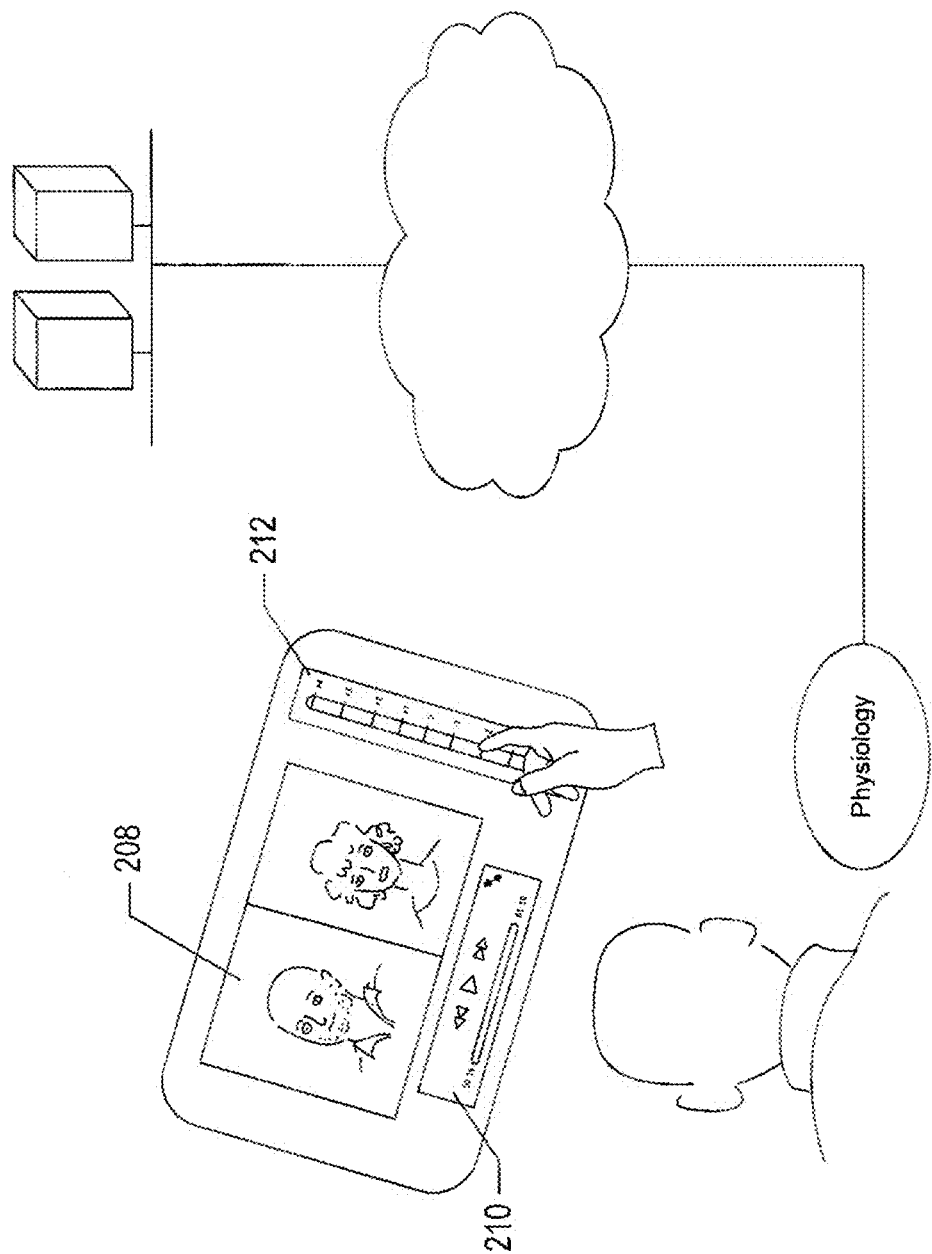

As shown in FIG. 2B, during the second-phase annotation sub-session, the first-phase discussion previously recorded during the initial phase of the relationship-analysis session is played back to the participant in split-screen mode 208. The participant is provided with playback controls 210 as well as a slidable rating feature 212 that the participant manipulates in order to input indications of varying degrees of positive and negative responses to what the participant is hearing and observing in the split-screen playback. The relationship-analysis-processing system collects the rating-feature inputs and physiological data and scales the collected data to the common timescale to which the audio and video-recording data are scaled. In certain implementations, the time scaling, or synchronization, of the data may be carried out following recording of the data by the relationship-analysis-processing system. In other implementations, at least an initial time scaling may be carried out as the data is collected. The participant ratings collected during the second-phase annotation sub-session represent subjective observation data that is subsequently used for relationship analysis.

Additionally, in many implementations, objective observation data is collected from human evaluators, automated observation systems, or from both. The previously recorded first-phase discussion is annotated with encoded indications of the types of behaviors exhibited by the participants during the discussion. Certain types of behavioral encodings provide indications of the likely emotional states of the participants as evidenced by their tone of voice, expressions, body positions, physiological data, and the semantic content of their vocal expressions.

Thus, by "subjective observation data," the current document means the rating annotations self-reported by participants and, by "subjective observation data," the current document means the evaluations embodied in the behavioral encodings provided by one or more of human evaluators and automated observation systems. In both cases, the ratings and behavioral encodings represent data values and these data values are associated with time points within the recorded first-phase discussion.

Figure 2C:
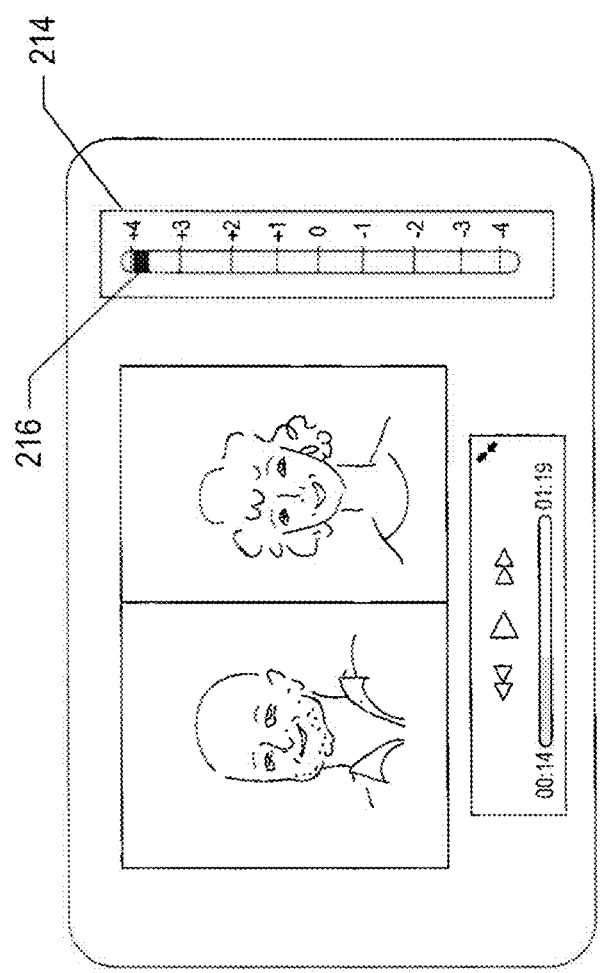
Figure 2D:
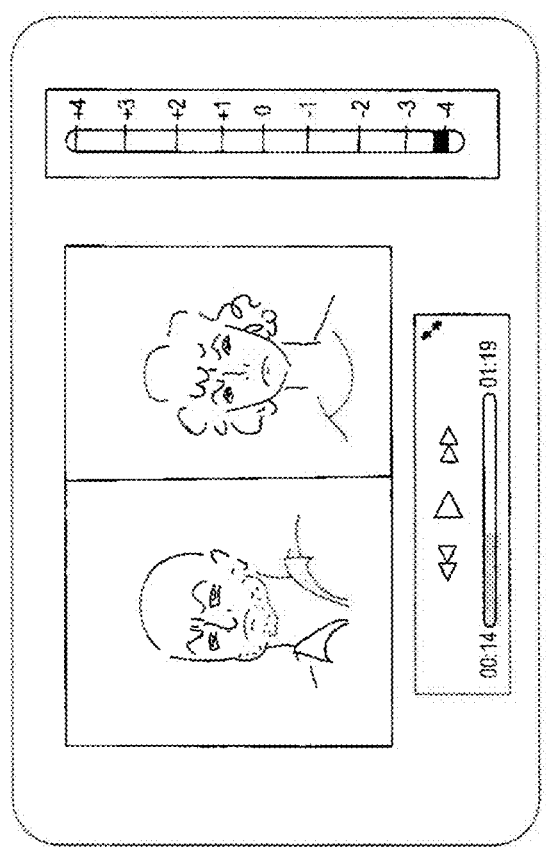

FIG. 2C shows the annotation-session display at a larger scale. The slidable rating feature 214, in the implementation shown in FIG. 2C, continuously ranges from a positive plus 4 to a negative minus 4. The position of the slider 216 is at the extreme position of the positive range, in FIG. 2C, while, in FIG. 2D, the slider 216 is at the extreme negative position of the negative range. Once the playback of the previously recorded discussion has finished, and the physiological data and slidable-rating-feature data have been collected, the second-phase annotation sub-session terminates. The second-phase annotation sub-session may be completed at different times by the two participants. In other implementations, the rating-dial ranges from 1.0 to 10.0. The rating-dial data may be subsequently remapped to alternative value ranges, as discussed below.

Figure 2E:
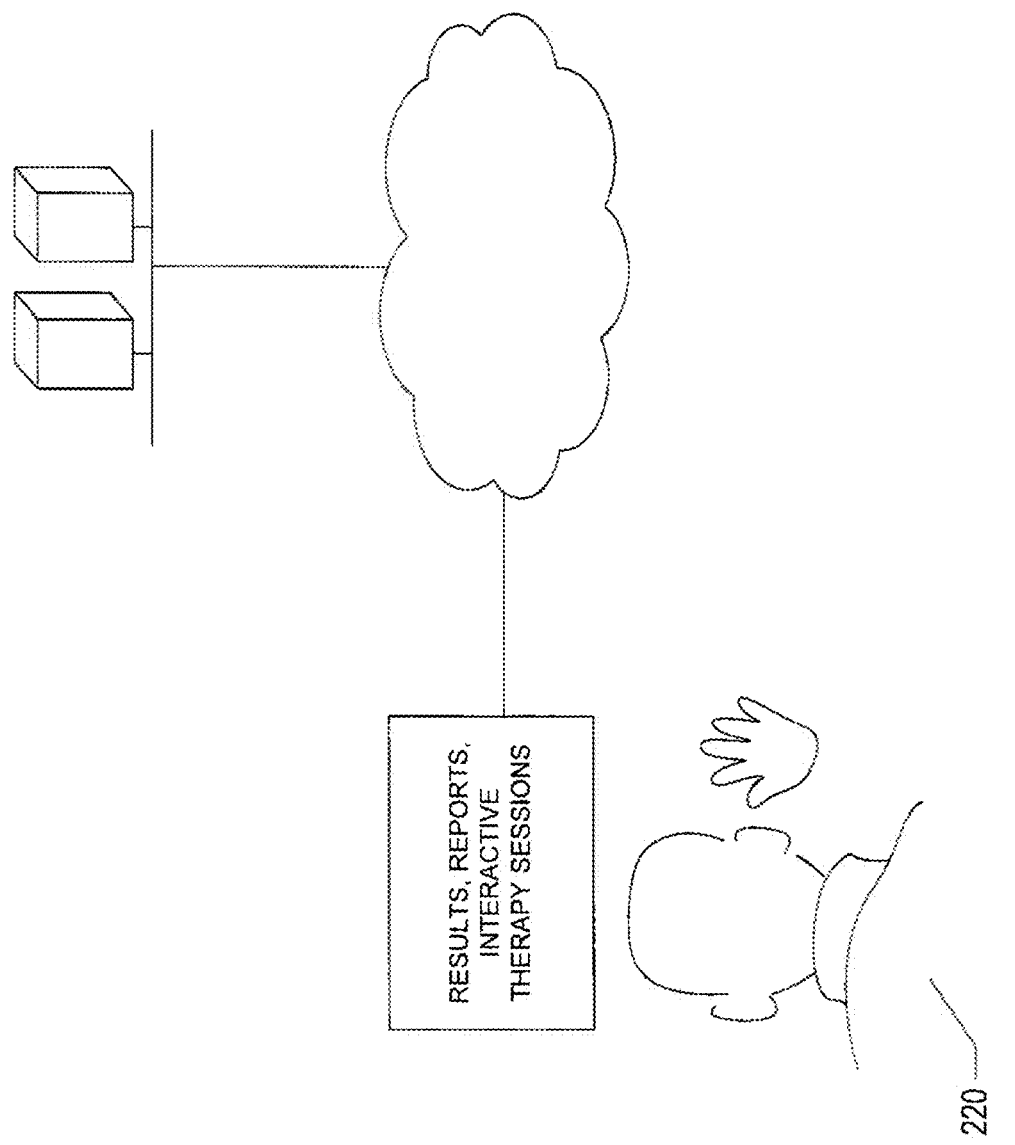
FIG. 2E illustrates a third phase of a relationship-analysis session.

FIG. 2E illustrates a third phase of a relationship-analysis session. In the third phase, a participant 220 logs back into the relationship-analysis application or connects to relationship-analysis services provided by the web server in order to receive results, reports, and, in certain cases, interactive therapy sessions with an automated counselor or a human evaluator. Again, the results, reports, and interactive sessions are displayed to the participant's video-enabled electronic device. The third phase of the relationship-analysis session generally occurs after a significant period of time has elapsed since completion of the second phase of relationship analysis by both participants. The elapsed time allows the relationship-analysis-processing system to fully scale the various different inputs, signals, and collected data to a common timescale, allows for execution of complex data-analysis and machine-learning subsystems, and, in certain implementations, may allow time for human-evaluator review of the results in preparation for report and result in generation and/or interactive therapy sessions.

Figure 3:
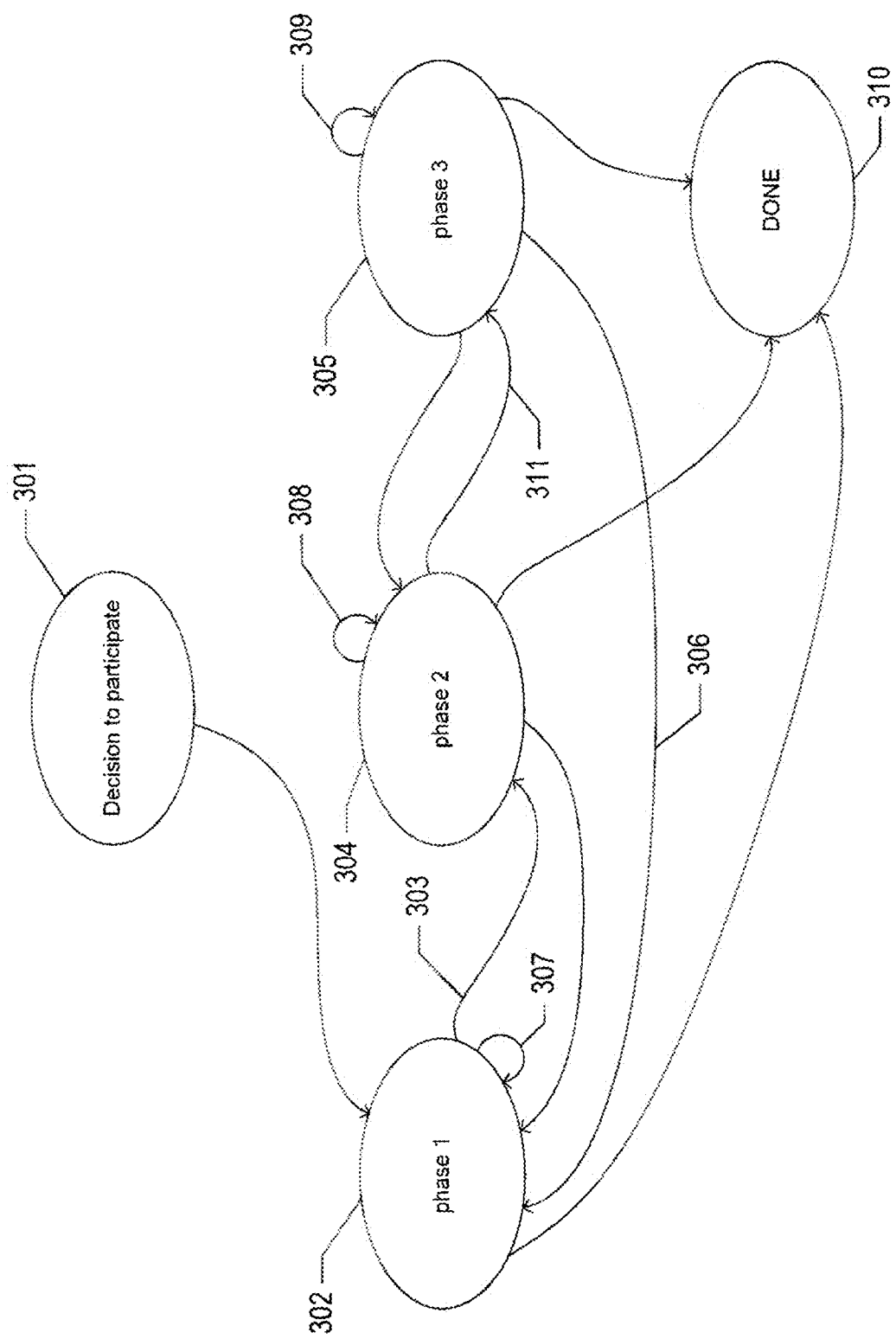
FIG. 3 shows a simple state-transition diagram for relationship counseling.

FIG. 3 shows a simple state-transition diagram for relationship analysis that is facilitated and partially automated by the disclosed semi-automated, distributed, interactive relationship-counseling system. A starting state 301 represents a pre-analysis state for a pair of participants who have decided to undertake relationship analysis. At some point in time, the participants initiate the initial-phase discussion, represented by state 302. When the initial phase is successfully completed, a transition 303 to a second-phase annotation-sub-session state 304 may occur. This is a bifurcated state, in that both participants need to separately complete the second-phase annotation sub-session before a transition 311 to the third-phase state 305 can occur. Depending on the types of reports and advice received by the participants, the participants may elect to transition 306 back to the first-phase state 302 in order to undertake a subsequent relationship-analysis session. Of course, during any particular relationship-analysis phase, interruptions and problems may arise, in which case that phase may be restarted from the beginning or from an interruption point, as represented by transitions 307-309. Eventually, when the participants have satisfied their goals in undertaking relationship analysis, the participants may transition to a terminal state 310. Of course, participants may elect to discontinue relationship analysis during any of the three phases of a relationship-analysis session.

Figure 4B:
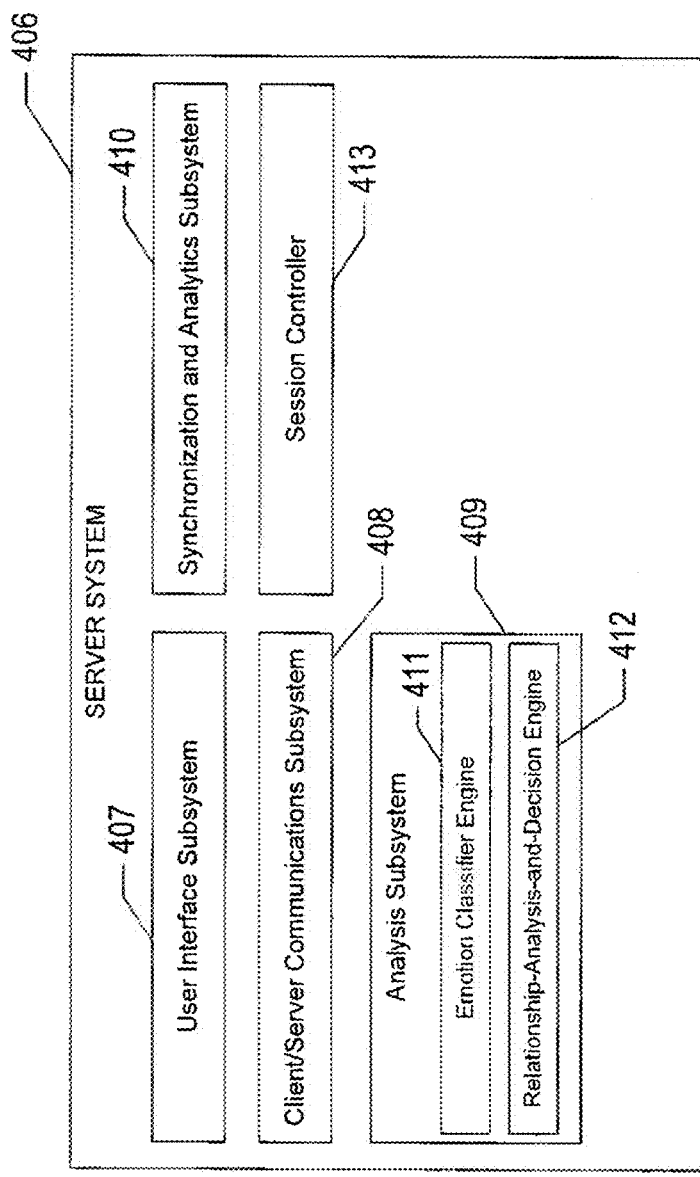
Figure 4C:
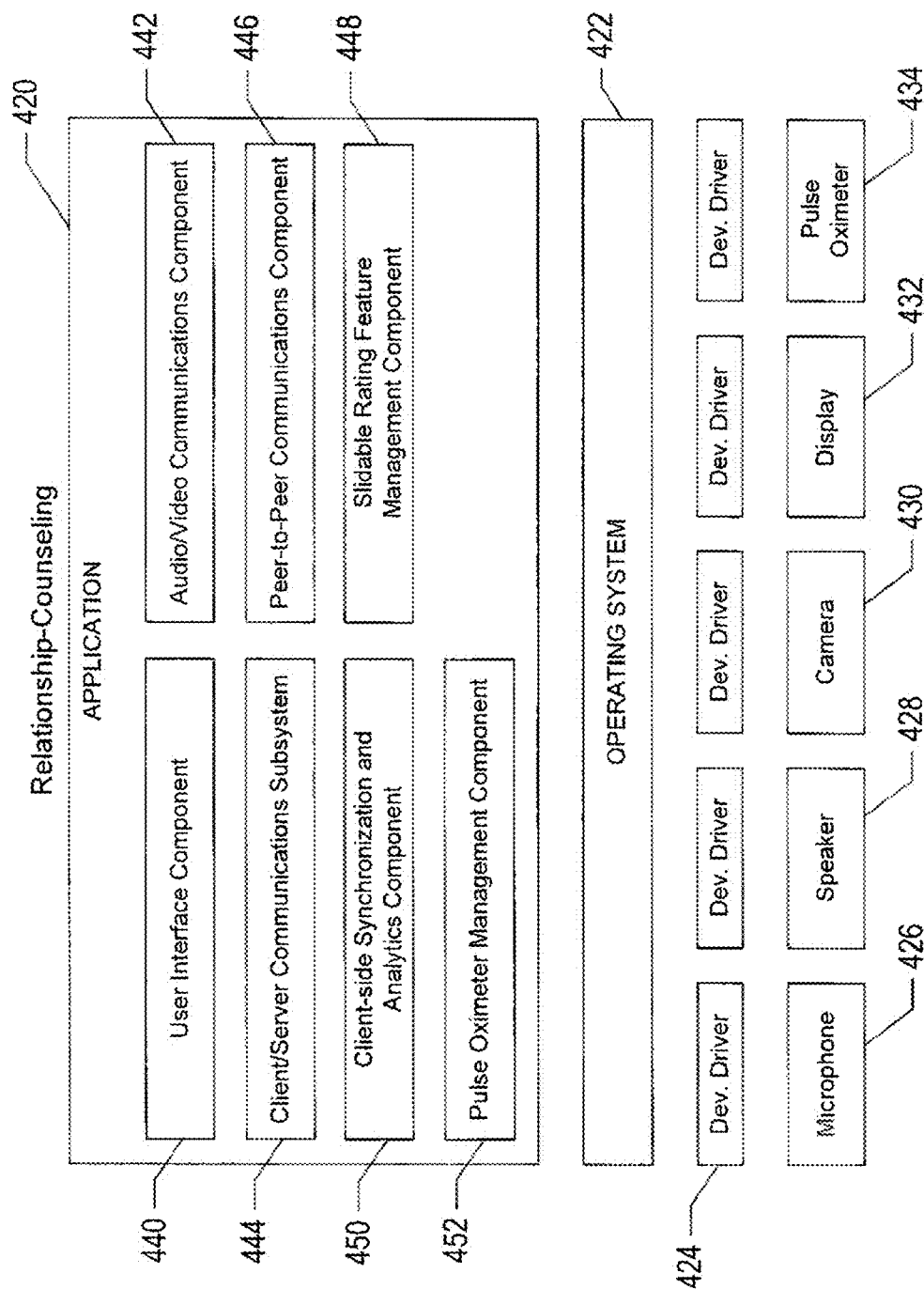

Overview of the System Architecture for One
Implementation of the Semi-Automated,
Distributed, Interactive Relationship-Counseling
System FIGS. 4A-C illustrate an architecture for one implementation of the semi-automated, distributed, interactive relationship-counseling system ("SDIRCS"). As shown in FIG. 4A, in a simple implementation, the semi-automated, distributed, interactive relationship-counseling system includes one or more servers 402, in many implementations resident within a cloud-computing facility, and two video-enabled participant electronic devices 403 and 404. As indicated by cloud symbol 405, the servers and video-enabled participant electronic devices are interconnected through electronic communications. In certain embodiments, the participants share a single video-enabled participant electronic device.

FIG. 4B shows a block diagram of a server in a single-server implementation.

The server 406 includes a user-interface subsystem 407, a communications subsystem 408 that provides for electronic communications with the two video-enabled participant electronic devices, a server-side timing-and-synchronization-management component 414, a relationship-analysis subsystem 409, and a synchronization and analytic subsystem 410. The analysis subsystem 409 includes an emotion-classifier engine 411 and a relationship-analysis-and-decision engine 412. A session controller 413 cooperates with the user-interface subsystem 407 and the communications subsystem 408 to control initial-phase discussions and second-phase annotation sub-sessions.

FIG. 4C provides a block diagram for a video-enabled participant electronic device. The video-enabled participant electronic device includes a relationship-analysis application 420 that executes in an execution environment provided by the device operating system 422. The device operating system includes multiple device drivers, such as device driver 424, that control operation of a microphone 426, a speaker 428, one or more video cameras 430, a display 432, one or more physiology sensors 434, rating dial 436, and a clock 438. The relationship-analysis application includes a user-interface component 440, an audio/video communications component 442, a client/server communications component 444, a peer-to-peer communications component 446, a slidable-rating-feature-management component 448, a client-side synchronization and analytics component 450, a pulse oximeter management component 452, and a client-side timing-and-synchronization-management component 454. Additional components may be included to manage other types of physiology sensors. The client/server communications component 444 manages communications with the relationship-analysis server or servers and the peer-to-peer communications component 446 manages communications with a partner participant's video-enabled electronic device.

Additional Implementations and Applications

The semi-automated, distributed, interactive relationship-counseling system ("SDIRCS") is discussed in the previous subsection as an example of a relationship-evaluation-and-relationship-management system that employs a relationship-analysis system. The above-discussed relational-analysis-processing system is one example of the currently disclosed relationship-analysis system. The relational-analysis-processing system produces trust metrics for each of the participants, in one implementation, that provide a basis for generation of many additional metrics and values related to the participants' relationship and may also provide a basis for control of subsequent actions and operations.

In many cases, a relationship-analysis system is implemented as a distributed system that executes across multiple discrete computer systems. It is possible for a relationship-analysis system to be implemented within a single computer system, as well.

There are many additional types of relationship-evaluation and relationship-management systems that employ various different implementations of the currently disclosed relationship-analysis system. For example, complex negotiations between representatives of organizations may be monitored by a relationship-evaluation-and-relationship-management system that provides feedback and suggestions to the negotiators following each stage of the complex negotiation. The negotiation-monitoring system may include automated monitoring subsystems that provide objective data and may include self-reporting subsystems that allow the negotiators to provide subjective data. The relationship-analysis system analyzes the most recent stage of the negotiation to produce trust metrics that quantify the trust held by each negotiating party for the other party. These trust metrics serve as a basis for determining many additional types of metrics and values used to summarize the relationship between the parties and to provide suggestions to the parties for future behaviors and strategies to facilitate the parties' negotiation goals. For example, when the mutual trust is high, the parties may be more willing to reveal their respective intents and to offer concessions the next round of negotiations. By contrast, when one of the parties appears to distrust the other party, the other party may consider providing additional information or taking other steps to increase that trust during the next round of negotiations. As another example, various types of on-line product and service providers may employ a relationship-evaluation-and-relationship-management system to evaluate the relationship between the on-line provider and a client or user based on interactions of the client or user with the on-line providers website, including previous and ongoing transactions. The relationship-evaluation-and-relationship-management system can provide evaluations and suggestions to the on-line provider for offerings and strategies, particular to the client or user, that will facilitate increased sales of services and/or products to the user or client. As yet another example, on-line education providers may employ relationship-evaluation-and-relationship-management systems to monitor the effectiveness of information transfer to particular on-line-education students. As more types of human activities and interactions are conducted in networked computing environments, there are will be increasing need and demand for many additional types of relationship-evaluation-and-relationship-management systems.

Computer Hardware, Complex Computational
Systems, and Virtualization

Figure 5:
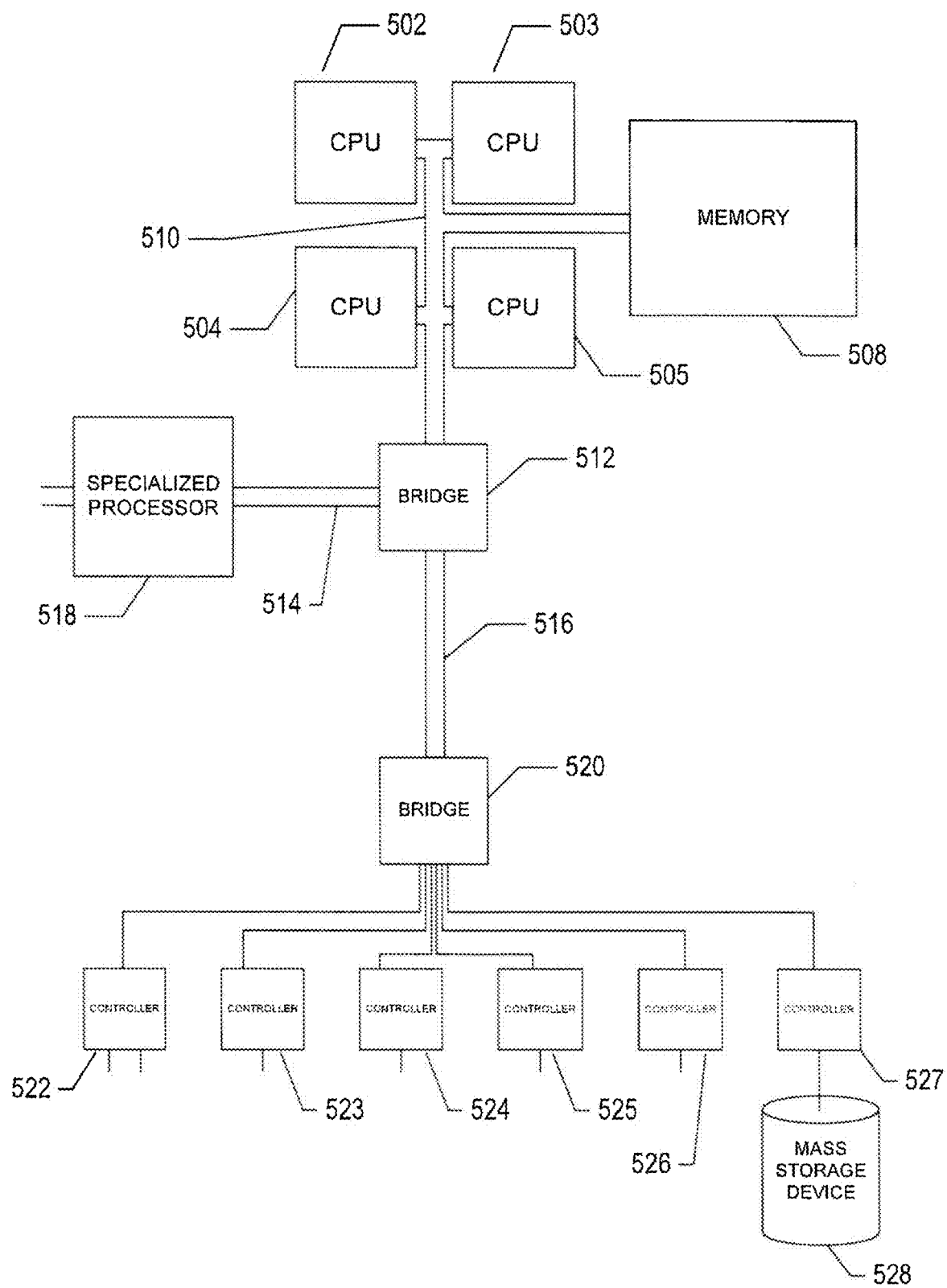
FIG. 5 provides a general architectural diagram for various types of computers.

FIG. 5 provides a general architectural diagram for various types of computers. The computer system contains one or multiple central processing units ("CPUs") 502-505, one or more electronic memories 508 interconnected with the CPUs by a CPU/memory-subsystem bus 510 or multiple busses, a first bridge 512 that interconnects the CPU/memory-subsystem bus 510 with additional busses 514 and 516, or other types of high-speed interconnection media, including multiple, high-speed serial interconnects. These busses or serial interconnections, in turn, connect the CPUs and memory with specialized processors, such as a graphics processor 518, and with one or more additional bridges 520, which are interconnected with high-speed serial links or with multiple controllers 522-527, such as controller 527, that provide access to various different types of mass-storage devices 528, electronic displays, input devices, and other such components, subcomponents, and computational resources. It should be noted that computer-readable data-storage devices include optical and electromagnetic disks, electronic memories, and other physical data-storage devices. Those familiar with modern science and technology appreciate that electromagnetic radiation and propagating signals do not store data for subsequent retrieval and can transiently "store" only a byte or less of information per mile, far less information than needed to encode even the simplest of routines.

Of course, there are many different types of computer-system architectures that differ from one another in the number of different memories, including different types of hierarchical cache memories, the number of processors and the connectivity of the processors with other system components, the number of internal communications busses and serial links, and in many other ways. However, computer systems generally execute stored programs by fetching instructions from memory and executing the instructions in one or more processors. Computer systems include general-purpose computer systems, such as personal computers ("PCs"), various types of servers and workstations, and higher-end mainframe computers, but may also include a plethora of various types of special-purpose computing devices, including data-storage systems, communications routers, network nodes, tablet computers, and mobile telephones.

Figure 6:
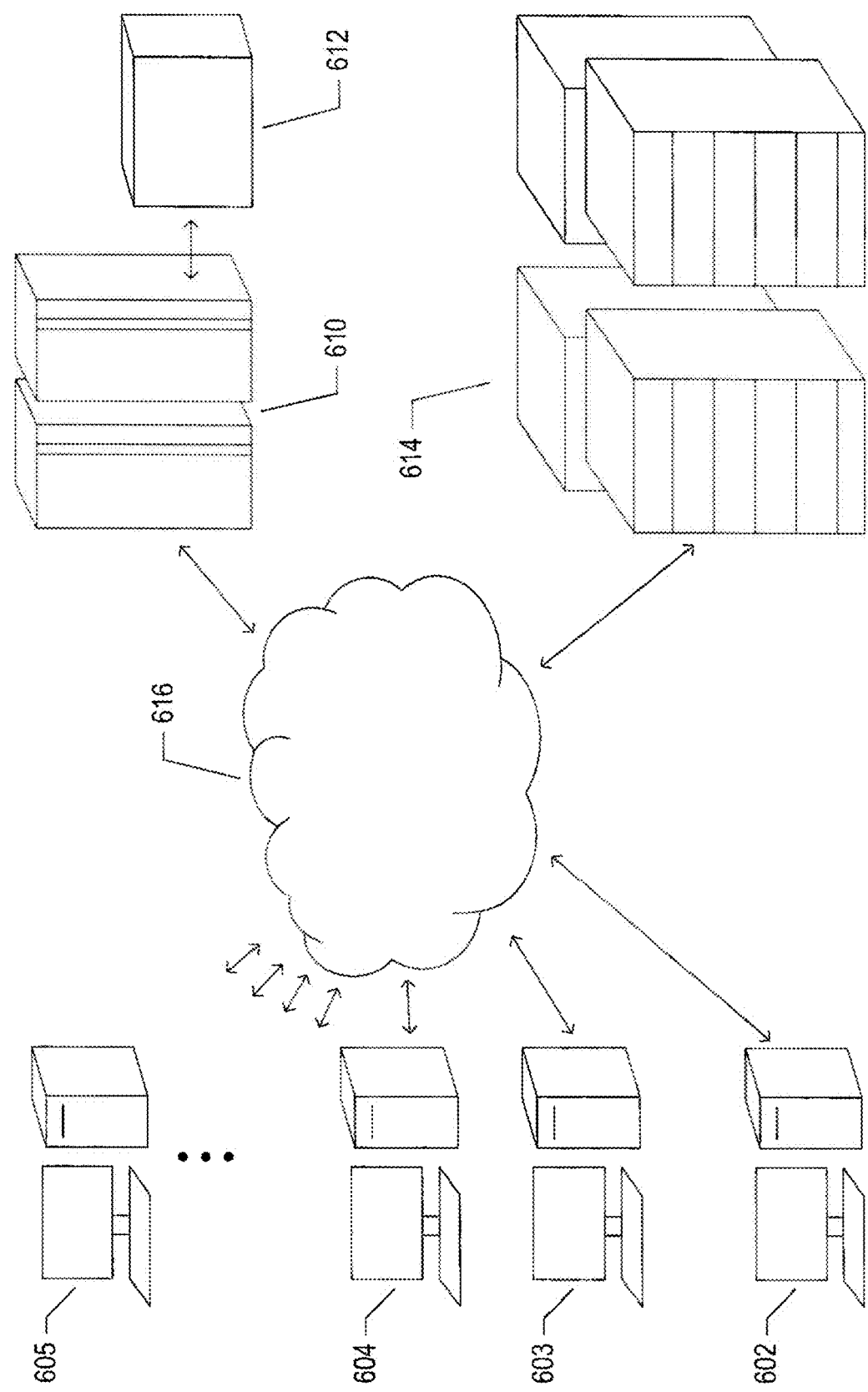
FIG. 6 illustrates an Internet-connected distributed computing system.

FIG. 6 illustrates an Internet-connected distributed computing system. As communications and networking technologies have evolved in capability and accessibility, and as the computational bandwidths, data-storage capacities, and other capabilities and capacities of various types of computer systems have steadily and rapidly increased, much of modern computing now generally involves large distributed systems and computers interconnected by local networks, wide-area networks, wireless communications, and the Internet. FIG. 6 shows a typical distributed system in which a large number of PCs 602-605, a high-end distributed mainframe system 610 with a large data-storage system 612, and a large computer center 614 with large numbers of rack-mounted servers or blade servers all interconnected through various communications and networking systems that together comprise the Internet 616. Such distributed computing systems provide diverse arrays of functionalities. For example, a PC user sitting in a home office may access hundreds of millions of different web sites provided by hundreds of thousands of different web servers throughout the world and may access high-computational-bandwidth computing services from remote computer facilities for running complex computational tasks.

Until recently, computational services were generally provided by computer systems and data centers purchased, configured, managed, and maintained by service-provider organizations. For example, an e-commerce retailer generally purchased, configured, managed, and maintained a data center including numerous web servers, back-end computer systems, and data-storage systems for serving web pages to remote customers, receiving orders through the web-page interface, processing the orders, tracking completed orders, and other myriad different tasks associated with an e-commerce enterprise.

Figure 7:
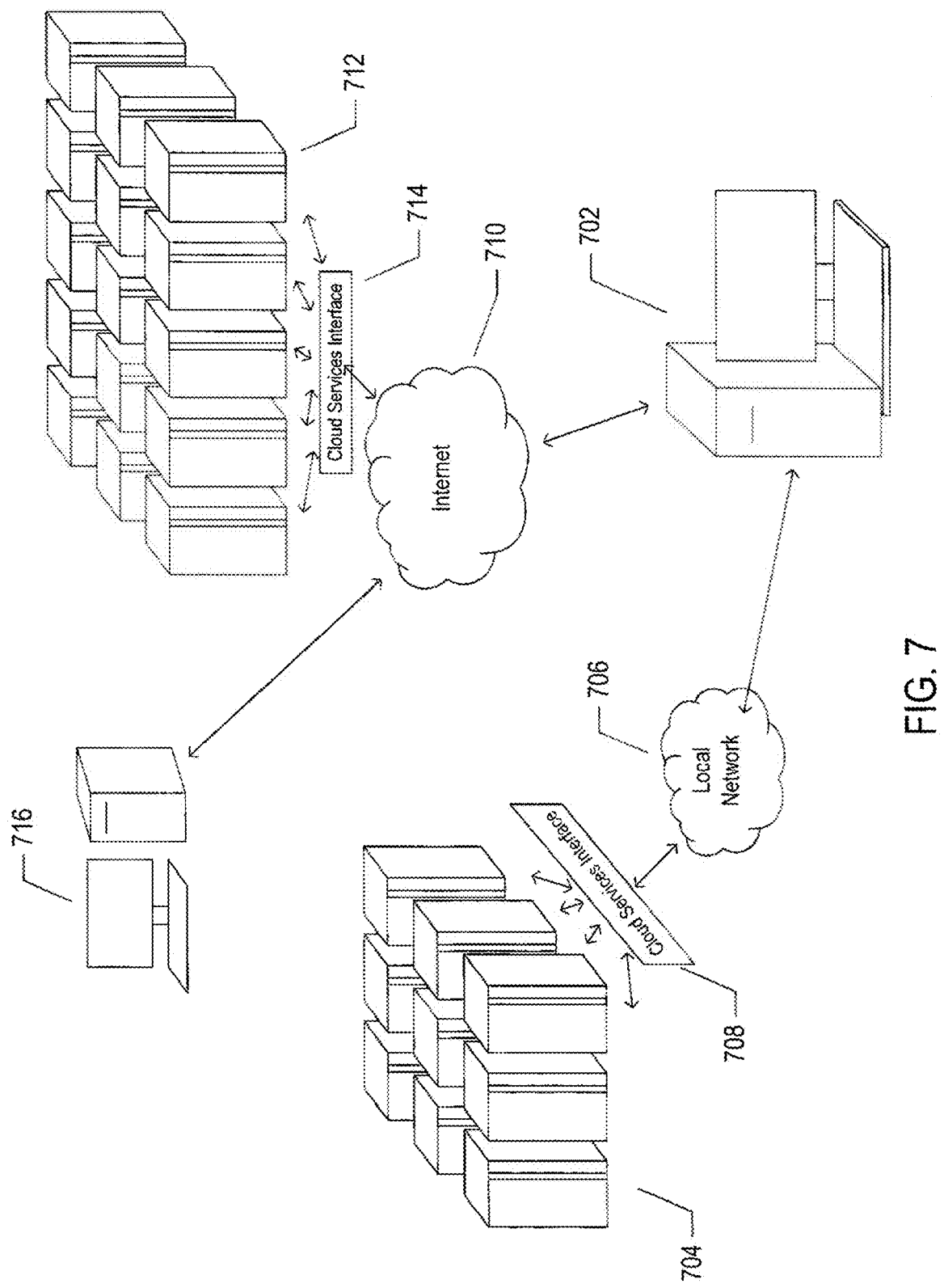
FIG. 7 illustrates cloud computing.

FIG. 7 illustrates cloud computing. In the recently developed cloud-computing paradigm, computing cycles and data-storage facilities are provided to organizations and individuals by cloud-computing providers. In addition, larger organizations may elect to establish private cloud-computing facilities in addition to, or instead of, subscribing to computing services provided by public cloud-computing service providers. In FIG. 7, a system administrator for an organization, using a PC 702, accesses the organization's private cloud 704 through a local network 706 and private-cloud interface 708 and also accesses, through the Internet 710, a public cloud 712 through a public-cloud services interface 714. The administrator can, in either the case of the private cloud 704 or public cloud 712, configure virtual computer systems and even entire virtual data centers and launch execution of application programs on the virtual computer systems and virtual data centers in order to carry out any of many different types of computational tasks. As one example, a small organization may configure and run a virtual data center within a public cloud that executes web servers to provide an e-commerce interface through the public cloud to remote customers of the organization, such as a user viewing the organization's e-commerce web pages on a remote user system 716.

Cloud-computing facilities are intended to provide computational bandwidth and data-storage services much as utility companies provide electrical power and water to consumers. Cloud computing provides enormous advantages to small organizations without the resources to purchase, manage, and maintain in-house data centers. Such organizations can dynamically add and delete virtual computer systems from their virtual data centers within public clouds in order to track computational-bandwidth and data-storage needs, rather than purchasing sufficient computer systems within a physical data center to handle peak computational-bandwidth and data-storage demands. Moreover, small organizations can completely avoid the overhead of maintaining and managing physical computer systems, including hiring and periodically retraining information-technology specialists and continuously paying for operating-system and database-management-system upgrades. Furthermore, cloud-computing interfaces allow for easy and straightforward configuration of virtual computing facilities, flexibility in the types of applications and operating systems that can be configured, and other functionalities that are useful even for owners and administrators of private cloud-computing facilities used by a single organization.

Figure 8:
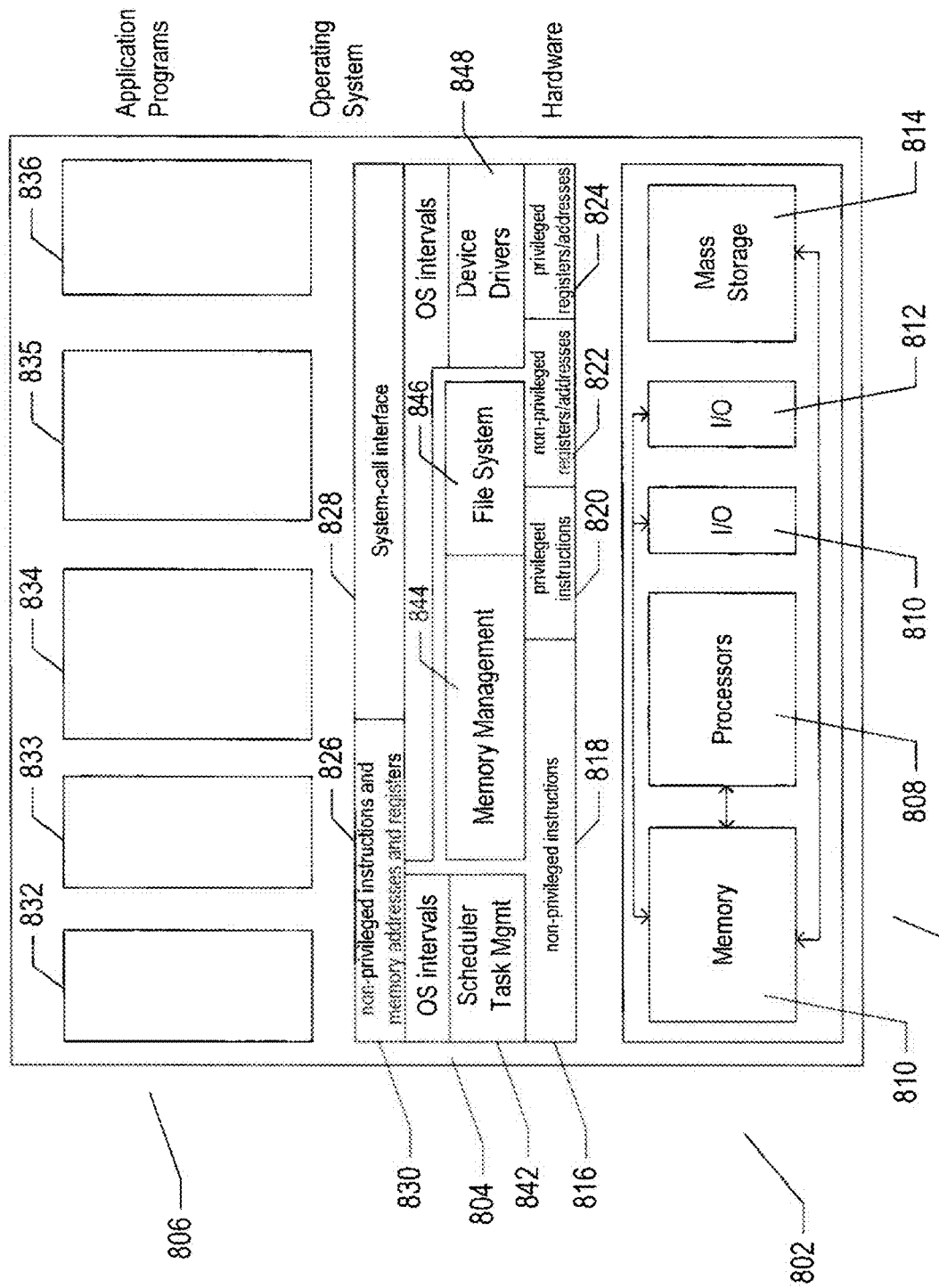
FIG. 8 illustrates generalized hardware and software components of a general-purpose computer system, such as a general-purpose computer system having an architecture similar to that shown in FIG. 1.

FIG. 8 illustrates generalized hardware and software components of a general-purpose computer system, such as a general-purpose computer system having an architecture similar to that shown in FIG. 5. The computer system 800 is often considered to include three fundamental layers: (1) a hardware layer or level 802; (2) an operating-system layer or level 804; and (3) an application-program layer or level 806. The hardware layer 802 includes one or more processors 808, system memory 810, various different types of input-output ("IO") devices 810 and 812, and mass-storage devices 814. Of course, the hardware level also includes many other components, including power supplies, internal communications links and busses, specialized integrated circuits, many different types of processor-controlled or microprocessor-controlled peripheral devices and controllers, and many other components. The operating system 804 interfaces to the hardware level 802 through a low-level operating system and hardware interface 816 generally comprising a set of non-privileged computer instructions 818, a set of privileged computer instructions 820, a set of non-privileged registers and memory addresses 822, and a set of privileged registers and memory addresses 824. In general, the operating system exposes non-privileged instructions, non-privileged registers, and non-privileged memory addresses 826 and a system-call interface 828 as an operating-system interface 830 to application programs 832-836 that execute within an execution environment provided to the application programs by the operating system. The operating system, alone, accesses the privileged instructions, privileged registers, and privileged memory addresses. By reserving access to privileged instructions, privileged registers, and privileged memory addresses, the operating system can ensure that application programs and other higher-level computational entities cannot interfere with one another's execution and cannot change the overall state of the computer system in ways that could deleteriously impact system operation. The operating system includes many internal components and modules, including a scheduler 842, memory management 844, a file system 846, device drivers 848, and many other components and modules. To a certain degree, modern operating systems provide numerous levels of abstraction above the hardware level, including virtual memory, which provides to each application program and other computational entities a separate, large, linear memory-address space that is mapped by the operating system to various electronic memories and mass-storage devices. The scheduler orchestrates interleaved execution of various different application programs and higher-level computational entities, providing to each application program a virtual, stand-alone system devoted entirely to the application program. From the application program's standpoint, the application program executes continuously without concern for the need to share processor resources and other system resources with other application programs and higher-level computational entities. The device drivers abstract details of hardware-component operation, allowing application programs to employ the system-call interface for transmitting and receiving data to and from communications networks, mass-storage devices, and other I/O devices and subsystems. The file system 836 facilitates abstraction of mass-storage-device and memory resources as a high-level, easy-to-access, file-system interface. Thus, the development and evolution of the operating system has resulted in the generation of a type of multi-faceted virtual execution environment for application programs and other higher-level computational entities.

While the execution environments provided by operating systems have proved to be an enormously successful level of abstraction within computer systems, the operating-system-provided level of abstraction is nonetheless associated with difficulties and challenges for developers and users of application programs and other higher-level computational entities. One difficulty arises from the fact that there are many different operating systems that run within various different types of computer hardware. In many cases, popular application programs and computational systems are developed to run on only a subset of the available operating systems and can therefore be executed within only a subset of the various different types of computer systems on which the operating systems are designed to run. Often, even when an application program or other computational system is ported to additional operating systems, the application program or other computational system can nonetheless run more efficiently on the operating systems for which the application program or other computational system was originally targeted. Another difficulty arises from the increasingly distributed nature of computer systems. Although distributed operating systems are the subject of considerable research and development efforts, many of the popular operating systems are designed primarily for execution on a single computer system. In many cases, it is difficult to move application programs, in real time, between the different computer systems of a distributed computing system for high-availability, fault-tolerance, and load-balancing purposes. The problems are even greater in heterogeneous distributed computing systems which include different types of hardware and devices running different types of operating systems. Operating systems continue to evolve, as a result of which certain older application programs and other computational entities may be incompatible with more recent versions of operating systems for which they are targeted, creating compatibility issues that are particularly difficult to manage in large distributed systems.

Figure 9A:
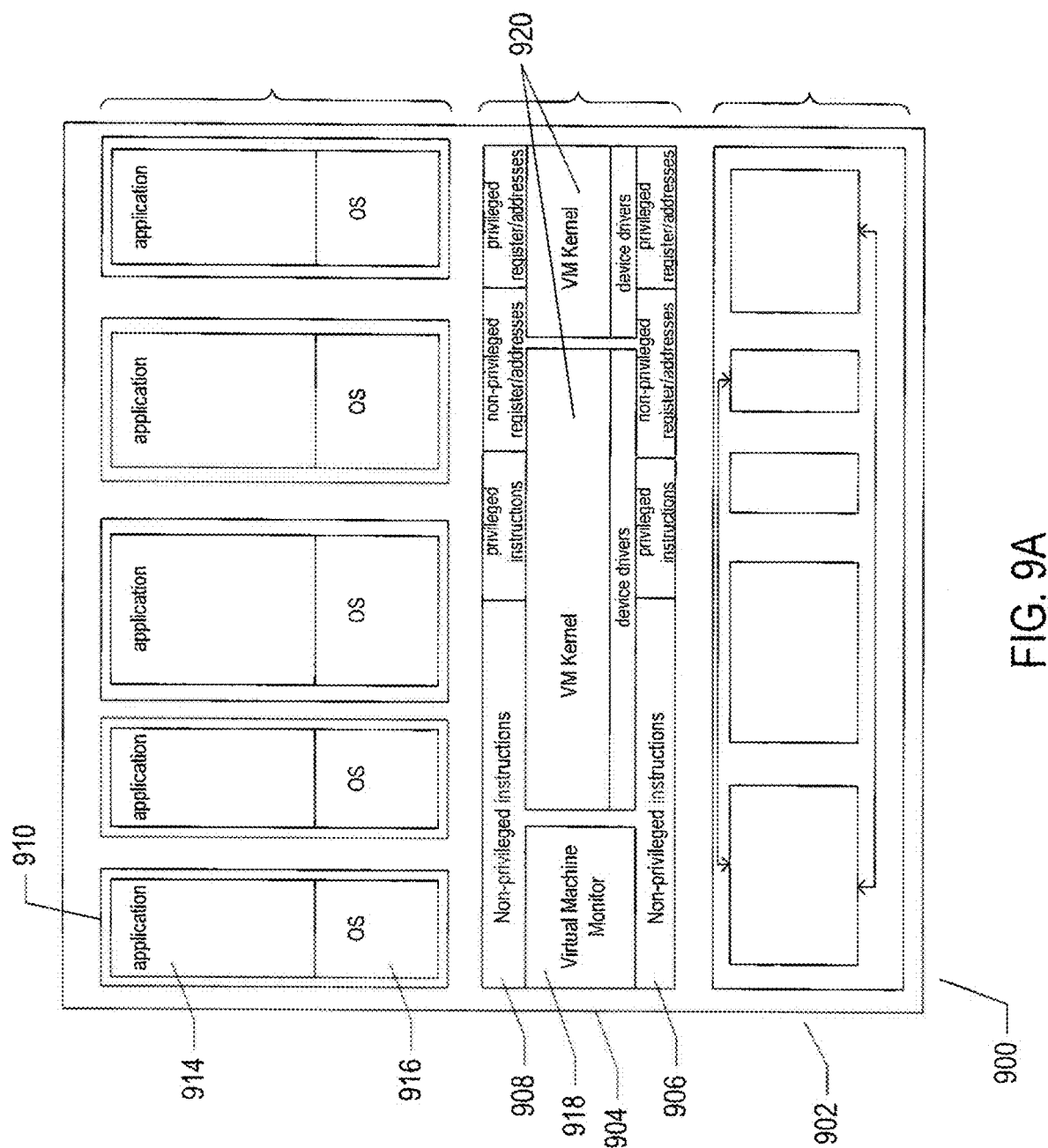
FIGS. 9A-B illustrate virtual machine and virtual-machine execution environments.
Figure 9B:
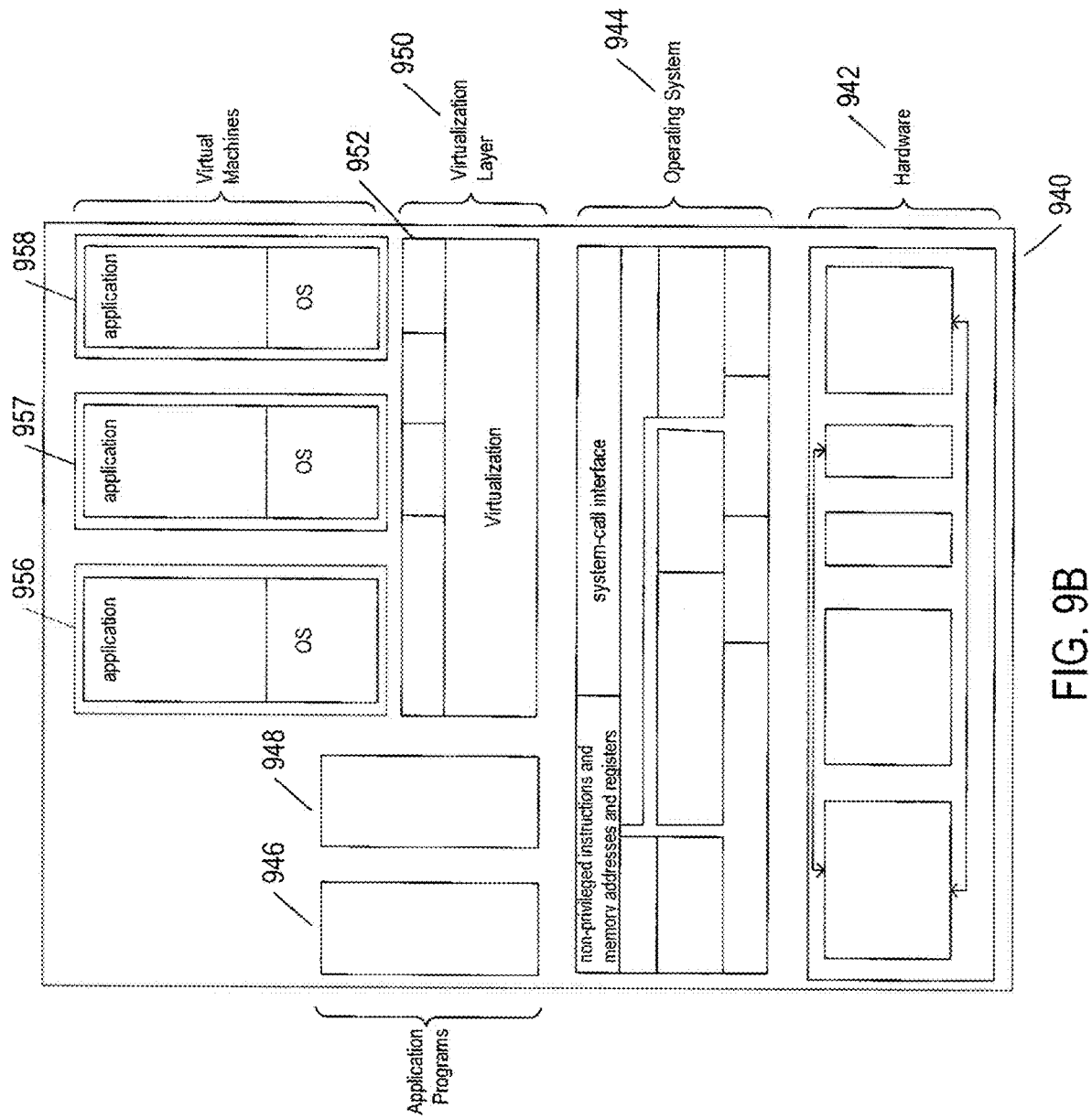

For all of these reasons, a higher level of abstraction, referred to as the "virtual machine," has been developed and evolved to further abstract computer hardware in order to address many difficulties and challenges associated with traditional computing systems, including the compatibility issues discussed above. FIGS. 9A-D illustrate several types of virtual machine and virtual-machine execution environments. FIGS. 9A-B use the same illustration conventions as used in FIG. 8. FIG. 9A shows a first type of virtualization. The computer system 900 in FIG. 9A includes the same hardware layer 902 as the hardware layer 802 shown in FIG. 8. However, rather than providing an operating system layer directly above the hardware layer, as in FIG. 8, the virtualized computing environment illustrated in FIG. 9A features a virtualization layer 904 that interfaces through a virtualization-layer, hardware-layer interface 906, equivalent to interface 816 in FIG. 8, to the hardware. The virtualization layer provides a hardware-like interface 908 to a number of virtual machines, such as virtual machine 910, executing above the virtualization layer in a virtual-machine layer 912. Each virtual machine includes one or more application programs or other higher-level computational entities packaged together with an operating system, referred to as a "guest operating system," such as application 914 and guest operating system 916 packaged together within virtual machine 910. Each virtual machine is thus equivalent to the operating-system layer 804 and application-program layer 806 in the general-purpose computer system shown in FIG. 8. Each guest operating system within a virtual machine interfaces to the virtualization-layer interface 908 rather than to the actual hardware interface 906. The virtualization layer partitions hardware resources into abstract virtual-hardware layers to which each guest operating system within a virtual machine interfaces. The guest operating systems within the virtual machines, in general, are unaware of the virtualization layer and operate as if they were directly accessing a true hardware interface. The virtualization layer ensures that each of the virtual machines currently executing within the virtual environment receive a fair allocation of underlying hardware resources and that all virtual machines receive sufficient resource to progress in execution. The virtualization-layer interface 908 may differ for different guest operating systems. For example, the virtualization layer is generally able to provide virtual hardware interfaces for a variety of different types of computer hardware. This allows, as one example, a virtual machine that includes a guest operating system designed for a particular computer architecture to run on hardware of a different architecture. The number of virtual machines need not be equal to the number of physical processors or even a multiple of the number of processors.

The virtualization layer includes a virtual-machine-monitor module 918 ("VMM") that virtualizes physical processors in the hardware layer to create virtual processors on which each of the virtual machines executes. For execution efficiency, the virtualization layer attempts to allow virtual machines to directly execute non-privileged instructions and to directly access non-privileged registers and memory. However, when the guest operating system within a virtual machine accesses virtual privileged instructions, virtual privileged registers, and virtual privileged memory through the virtualization-layer interface 908, the accesses result in execution of virtualization-layer code to simulate or emulate the privileged resources. The virtualization layer additionally includes a kernel module 920 that manages memory, communications, and data-storage machine resources on behalf of executing virtual machines ("VM kernel"). The VM kernel, for example, maintains shadow page tables on each virtual machine so that hardware-level virtual-memory facilities can be used to process memory accesses. The VM kernel additionally includes routines that implement virtual communications and data-storage devices as well as device drivers that directly control the operation of underlying hardware communications and data-storage devices. Similarly, the VM kernel virtualizes various other types of VO devices, including keyboards, optical-disk drives, and other such devices. The virtualization layer essentially schedules execution of virtual machines much like an operating system schedules execution of application programs, so that the virtual machines each execute within a complete and fully functional virtual hardware layer.

FIG. 9B illustrates a second type of virtualization. In FIG. 9B, the computer system 940 includes the same hardware layer 942 and software layer 944 as the hardware layer 802 shown in FIG. 8. Several application programs 946 and 948 are shown running in the execution environment provided by the operating system. In addition, a virtualization layer 950 is also provided, in computer 940, but, unlike the virtualization layer 904 discussed with reference to FIG. 9A, virtualization layer 950 is layered above the operating system 944, referred to as the "host OS," and uses the operating system interface to access operating-system-provided functionality as well as the hardware. The virtualization layer 950 comprises primarily a VMM and a hardware-like interface 952, similar to hardware-like interface 908 in FIG. 9A. The virtualization-layer/hardware-layer interface 952, equivalent to interface 816 in FIG. 8, provides an execution environment for a number of virtual machines 956-958, each including one or more application programs or other higher-level computational entities packaged together with a guest operating system.

The Trust Metric and a Trust-Metric-Generation Process

The current subsection of this document discusses trust metrics and one implementation of a trust-metric-generation process. As mentioned above, trust metrics provide a basis for generation of many different types of metrics and values by the different types of relationship-analysis systems incorporated within different types of relationship-evaluation-and-relationship-management systems. The following discussion uses, as an example, the semi-automated, distributed, interactive relationship-counseling system ("SDIRCS") and the relational-analysis-processing system incorporated within the SDIRCS. However, trust metrics can be generated by different types of relationship-analysis systems from different types of objective and subjective observation data.

FIG. 10 illustrates an example observation data set collected from a relationship-analysis session by the SDIRCS discussed in the preceding subsections of this document. Four different individual data sets 1002-1005 are shown in FIG. 10. Each of the individual data sets is represented as a 2-column table, with the left-hand column representing time points and the right-hand column representing data values. The individual data set 1002 contains the rating-dial-derived values corresponding to annotations to the recorded video for a first participant, participant P0, and the individual data set 1003 contains the rating-dial-derived values corresponding to annotations to the recorded video for a second participant, participant P1. The rating-dial-derived values are floating-point values in the range [1.0 to 10.0], with two-digit precision. The individual data set 1004 includes the objective observation data for the first participant, participant P0, and individual data set 1005 includes the objective observation data for the second participant, P. In this example, the data values for the two objective individual data sets are selected from the set {-1, 0, 1}, which can alternatively be represented by the set {-, 0, +} or the set {negative, neutral, positive}. As discussed further, below, these data values may be obtained by a mapping from a larger set of behavioral encodings. The first two individual data sets 1002 and 1003 are referred to as individual data sets S/P0 and S/P1, respectively, which stand for "self-reported data for participant P0" and "self-reported data for participant P1." The third and fourth individual data sets 1004 and 1005 are referred to as individual data sets O/P0 and O/P1, respectively, which stand for "objective data for participant P0" and "objective data for participant P1." The ellipses in FIG. 10, such as ellipses 1006, indicate that there are many additional time-point/value pairs, referred to as "data points," in the four tables. In this example, the first-phase discussion lasted for 20 minutes, and data points were collected at 1-second intervals.

Figure 11A:
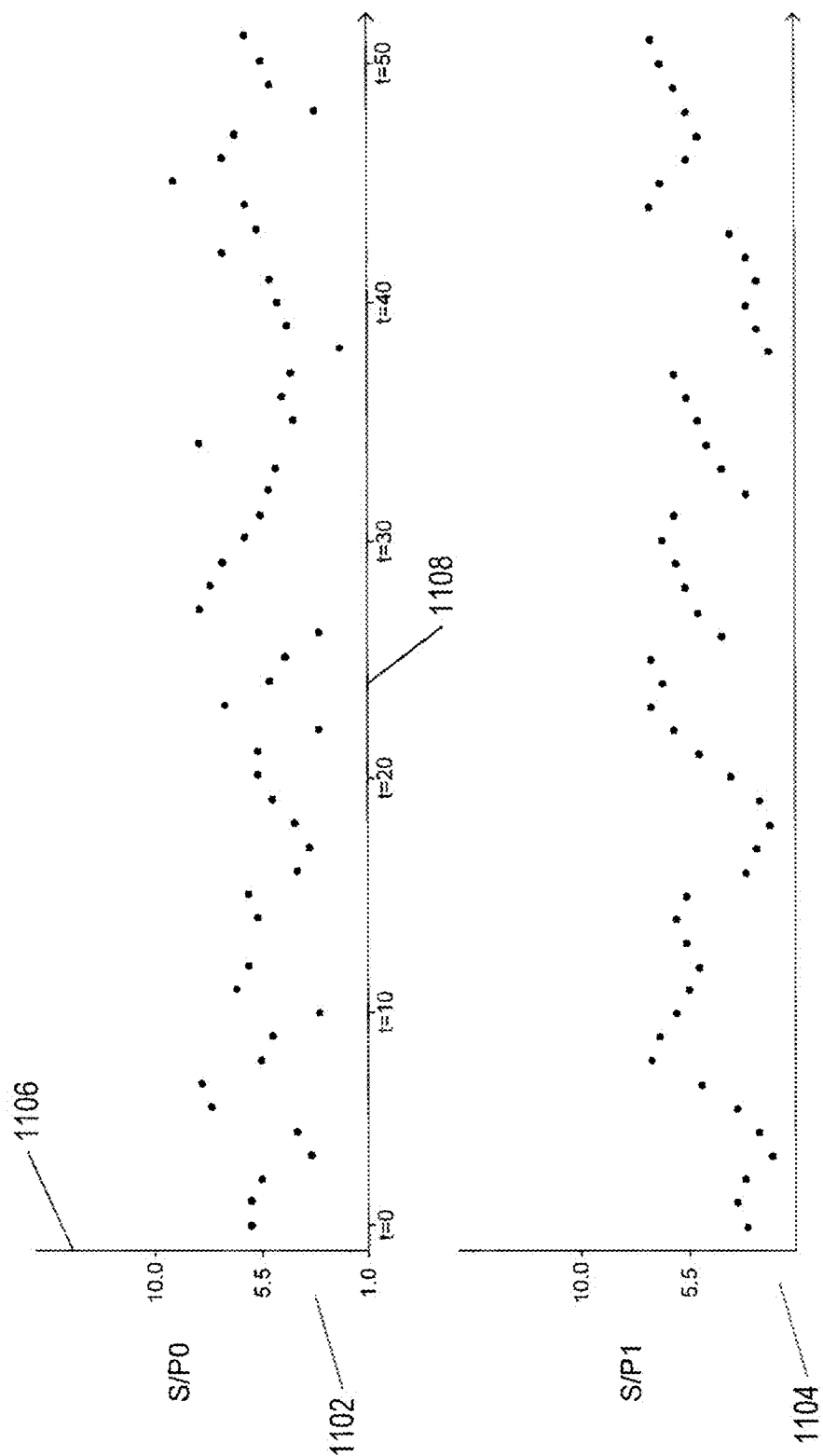
Figure 11B:
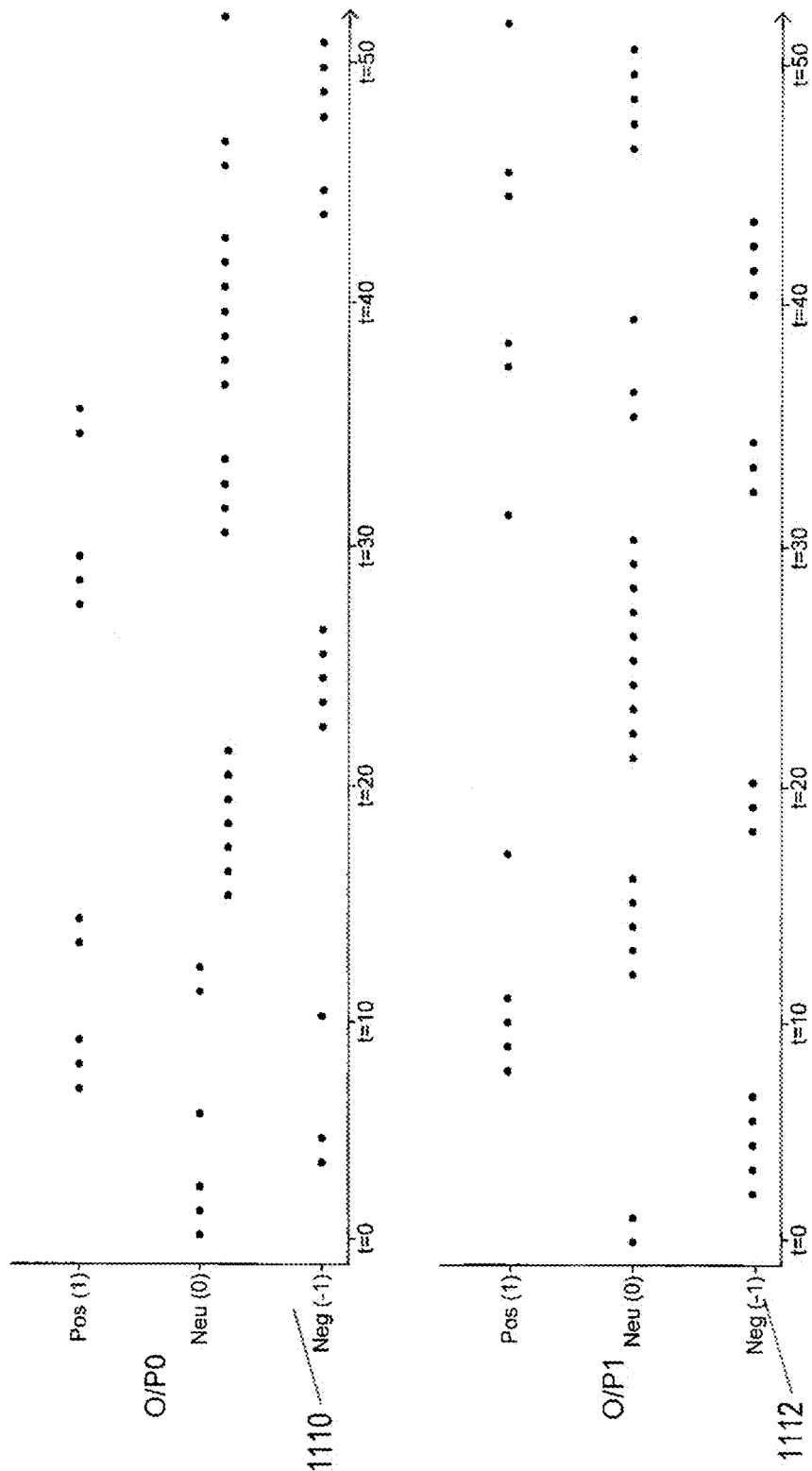

FIGS. 11A-B show 2-dimensional plots of the four individual data sets shown in FIG. 10. FIG. 11A shows a first plot 1102 of the individual data set S/P0 and a second plot 1104 of the individual data set S/P1. In each plot, the vertical axis, such as vertical axis 1106, represents the data value and the horizontal axis, such as horizontal axis 1108, represents time. FIG. 11B shows plots of the individual data set O/P0 1110 and the individual data set O/P1 1112.

FIG. 12 shows two alternative tabular representations of an observation data set comprising the initial 15 time-point/data-value pairs of the four individual data sets shown in FIG. 10 and plotted in FIGS. 11A-B. In these tables, the individual observation-data-set values, at each time point, are combined to form a context. The context is an ordered pair of observation-data-set values. Because there are three different data values in the individual observation-data-sets, there are $3^3=9$ different contexts: (−1, −1), (−1, 0), (−1, 1), (0, −1), (0, 0), (0,1), (1, −1), (1, 0), and (1, 1). These nine different contexts can be alternatively represented by the nine different observed-behavior contexts (negative, negative), (negative, neutral), (negative, positive), (neutral, negative), (neutral, neutral), (neutral, positive), (positive, negative), (positive, neutral), and (positive, positive). The first data value in a context corresponds to the objectively ascertained behavioral or emotional state of participant P0 and the second data value in the context corresponds to the objectively ascertained behavioral or emotional state of participant P1. Thus, context (positive, negative) indicates that, at the time point corresponding to the context, participant P0 was in a positive behavioral or emotional state and participant P1 was in a negative behavioral or emotional state. Only the first 15 time-point/data-value pairs of the four individual data sets are considered, in the example trust-metric computation, discussed below, for clarity of illustration. The example computation produces trust metrics based on only the first 15 seconds of data. In general, trust metrics can be computed for an entire first-phase discussion or for each of multiple portions of the first-phase discussion.

In the first table 1202 shown in FIG. 12, the data values for all four individual observation data sets at any given time point are shown in a row within the table. For example, the first row 1204 indicates that at time point 0, participant P0 self-reported a rating-dial value of 6.0, as seen in the middle column P0 1206, participant P self-reported a rating-dial value of 3.0, as seen in the rightmost column P1 1208, and the behavioral values were (0, 0), as shown in the leftmost column context 1210, indicating that both participants were in neutral behavioral or emotional states. Horizontal lines divide the rows into groups of rows having the same context within the table. Thus, the first two rows of the table 1204 and 1212 have the same context value (0, 0). The second table 1214 reorganizes the rows of the first table so that rows with a common context value are adjacent. This table is subdivided into blocks, by horizontal lines, such as horizontal line 1216, within each of which the rows have a common context value.

Figure 13:
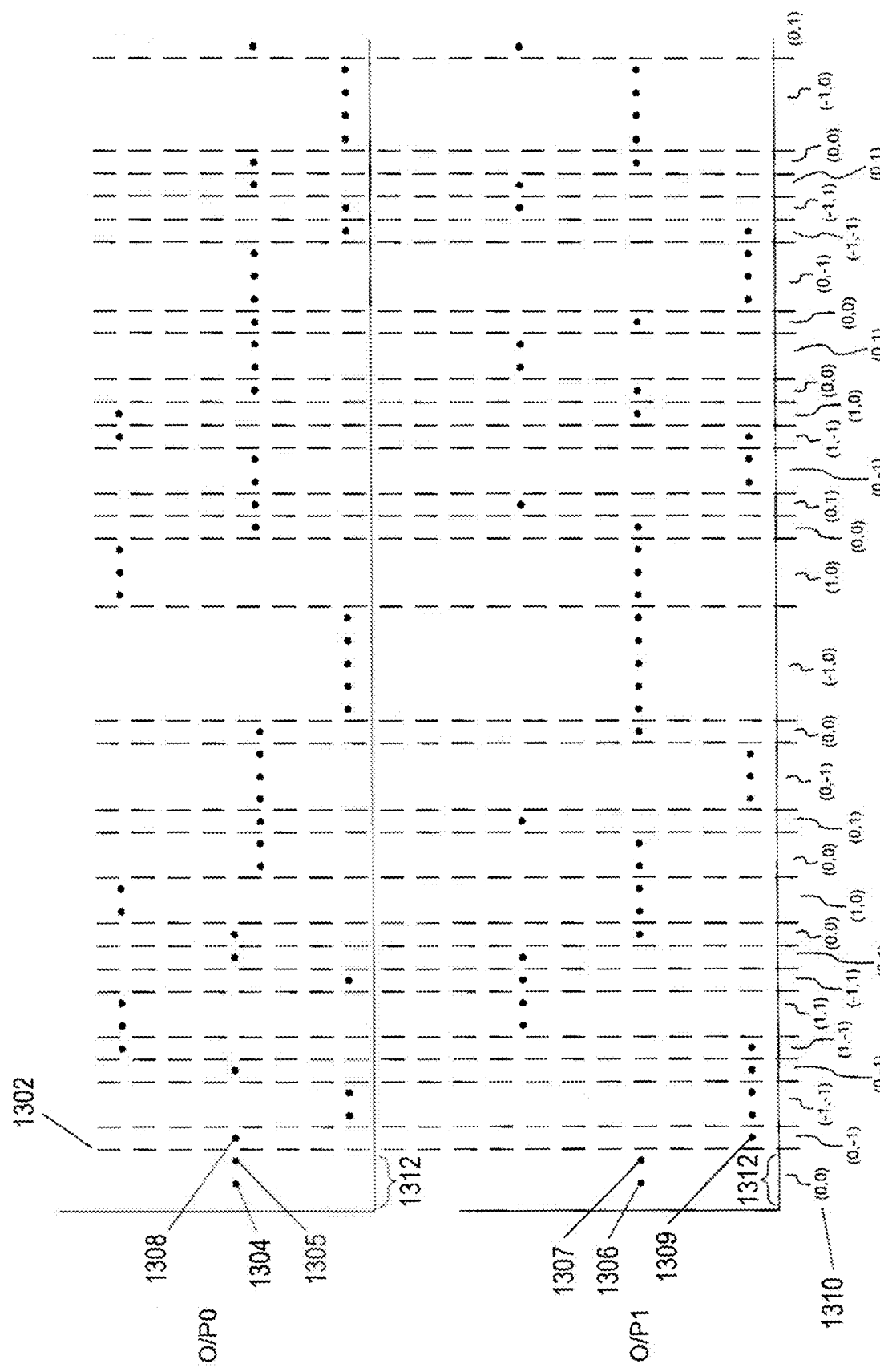
FIG. 13 shows the plots of the O/P0 and O/P1 individual data sets vertically aligned with vertical dashed lines indicating boundaries between different context values along the time axis.

FIG. 13 shows the plots of the O/P0 and O/P1 individual data sets vertically aligned with vertical dashed lines indicating boundaries between different context values along the time axis. For example, for the first two time values, the context value is (0,0), but, for the third time value, the context value is (0, −1). Thus, vertical dashed line 1302 is placed to separate the first two time-point/data-value points 1304-1307 in the two plots from the third time-point/data-value points 1308-1309. The context values for each portion of the time axes are shown below the lower plot, such as the context value (0, 0) 1310 for the first portion 1312 of the time axes between the origins of the time axes and the intersections of vertical dashed line 1302 with the time axes. Thus, the sequence of context values along the time axes shown in FIG. 13 corresponds to the sequence of context values in the first column of the first table shown in FIG. 12.

Figure 14:
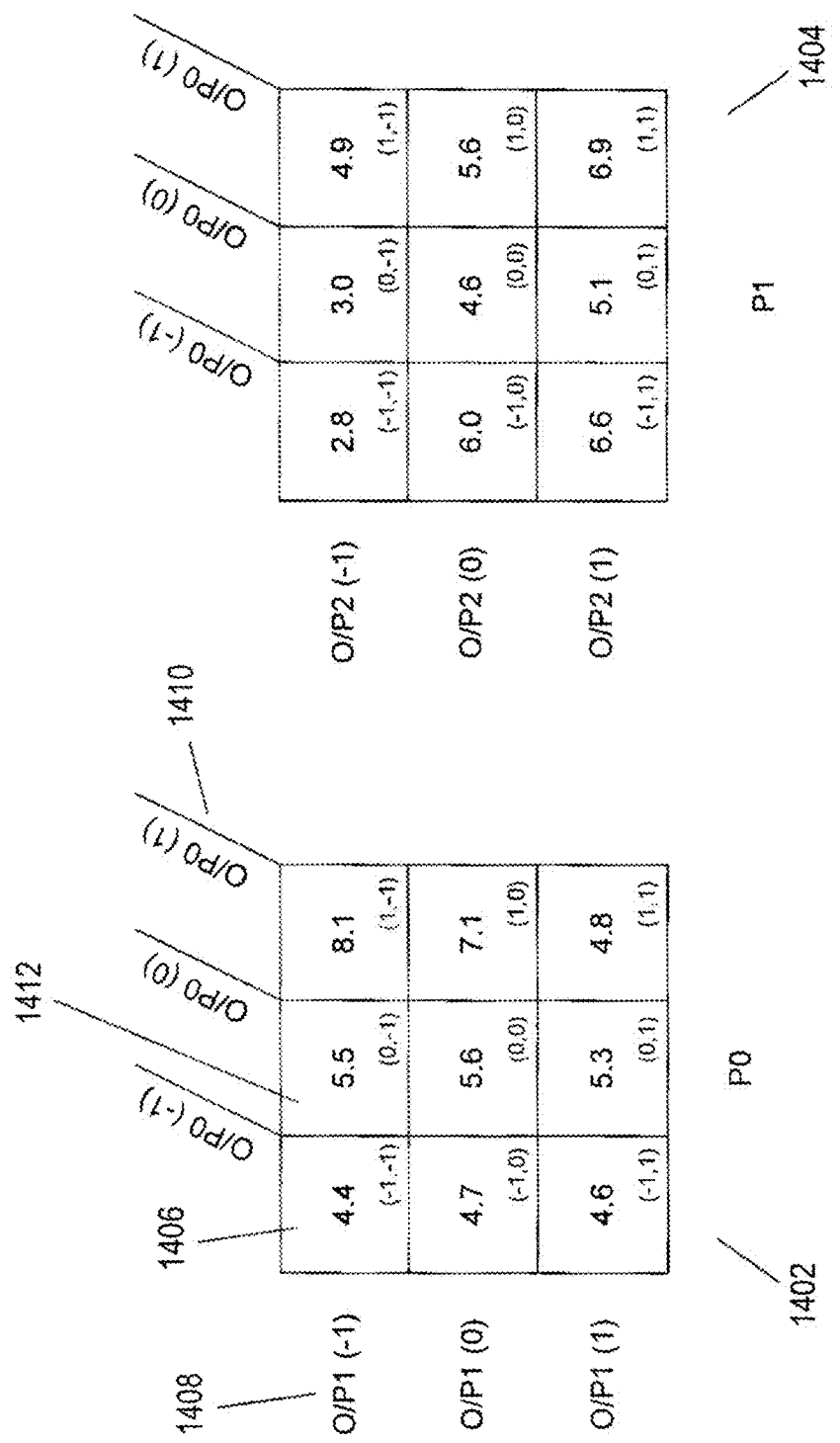
FIG. 14 illustrates two context-based preference matrices.

FIG. 14 illustrates two context-based preference matrices. The first context-based preference matrix 1402 stores the average rating-dial values reported by participant P0 during each of the nine different types of contexts and the second context-based preference matrix 1404 stores the average rating-dial values reported by participant P1 during each of the nine different types of contexts. For example, consider the top left cell 1406 in the first context-based preference matrix 1402. The rows in this context-based preference matrix correspond to fixed values for the objective behavioral or emotional state of participant P1 and the columns in this context-based preference matrix correspond to fixed values for the objective behavioral or emotional state of participant P0, as indicated by the row labels in the vertical column 1408 external to the context-based preference matrix 1402 and in the column labels in the horizontal row 1410 external to the context-based preference matrix 1402. Cell 1406 thus represents the context (−1, −1) or, alternatively expressed, (negative, negative). Cell 1406 thus contains the mean self-reported rating-dial value reported by participant P0 for those time points in which the objective behavioral or emotional state of both participants was negative. Referring back to FIG. 12, the value 4.4 in cell 1406 is the average of the three rating-dial values in cell 1220 of table 1214: (3.4-4.1+5.7)/3=4.4. Similarly, the value 5.5 in cell 1412 of the context-based preference matrix 1402 is the average value of the rating-dial values in cell 1222 of table 1214 in FIG. 12.

Figure 15:
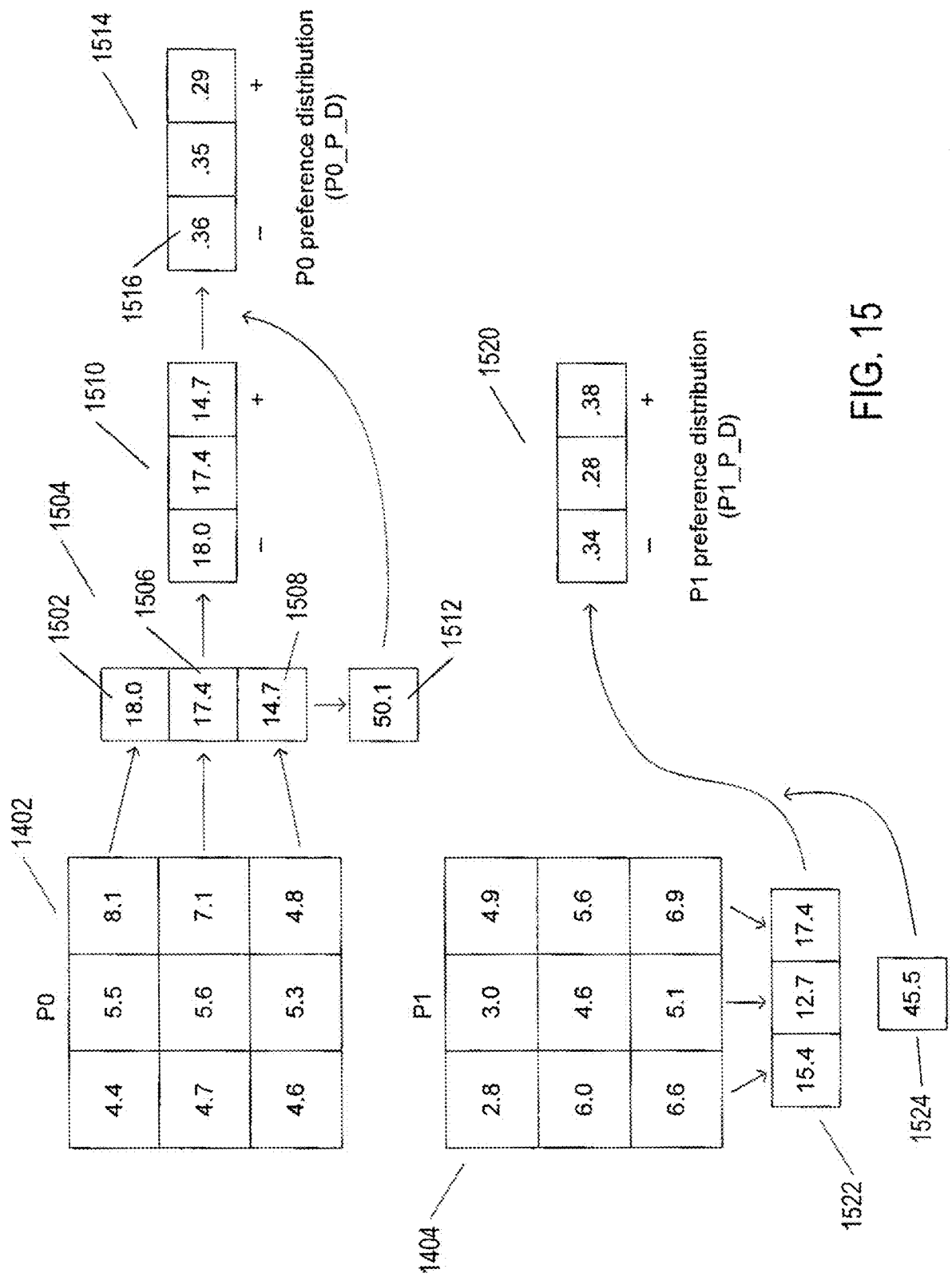
FIG. 15 illustrates generation of preference distributions for the two participants P0 and P1.

FIG. 15 illustrates generation of preference distributions for the two participants P0 and P1. A preference distribution is a probability distribution for a participant's behavioral or emotional state given a particular behavioral or emotional state of the other participant. The context-based preference matrix 1402 for participant P0 is again shown in FIG. 15. The values in the cells of the top row in this context-based preference matrix are summed, and the sum is entered in a top cell 1502 of a column vector 1504. Similarly, the sums of the values in the middle and lower rows of the context-based preference matrix 1402 are placed in the second 1506 and third 1508 cells of the column vector. The column vector is then transposed to generate a row vector 1510. The values in the three cells of the column vector are summed to produce a sum 1512. The value in each cell of the row vector 1510 is divided by the sum 1512 to produce a final preference distribution 1514 for participant P0. The preference distribution 1514 indicates the fractions of the sum of rating-dial indications self-reported by participant P0 reported by participant P0 for each of the behavioral or emotional states of participant P1. For example, 36% of the sum of rating-dial indications provided by participant P0 were self-reported at points in time during which participant P1 exhibited a negative behavioral or emotional state, as indicated by the value 0.36 in cell 1516 of the preference distribution 1514 for participant P0, referred to as P0_P_D in the following discussion. Because larger rating-dial values correspond to more favorable emotional states self-reported by participant P0, the P0_P_D provides an indication of the preference of participant P0 for the three different objectively determined behavioral or emotional states of participant P1 negative, neutral, positive). In this case, participant P0 appears to prefer negative and neutral behavioral or emotional states of participant P1 over a positive behavioral or emotional state of participant P1.

The preference distribution for participant P1 (1520) is similarly generated, as shown in the lower portion of FIG. 15. This preference distribution is referred to as P1_P_D in the following discussion. The sums of the values in the cells of each column of the context-based preference matrix 1404 for participant P1 are entered into the cells of row vector 1522. The sum of the values in the cells of the row vector is also calculated 1524. Division of the value in each cell of the row vector 1522 by the sum 1524 produces the preference distribution for participant P1 (1520). In the current example, participant P1 favors a positive behavioral or emotional state exhibited by participant P0 over neutral and negative behavioral or emotional states.

Figure 16:
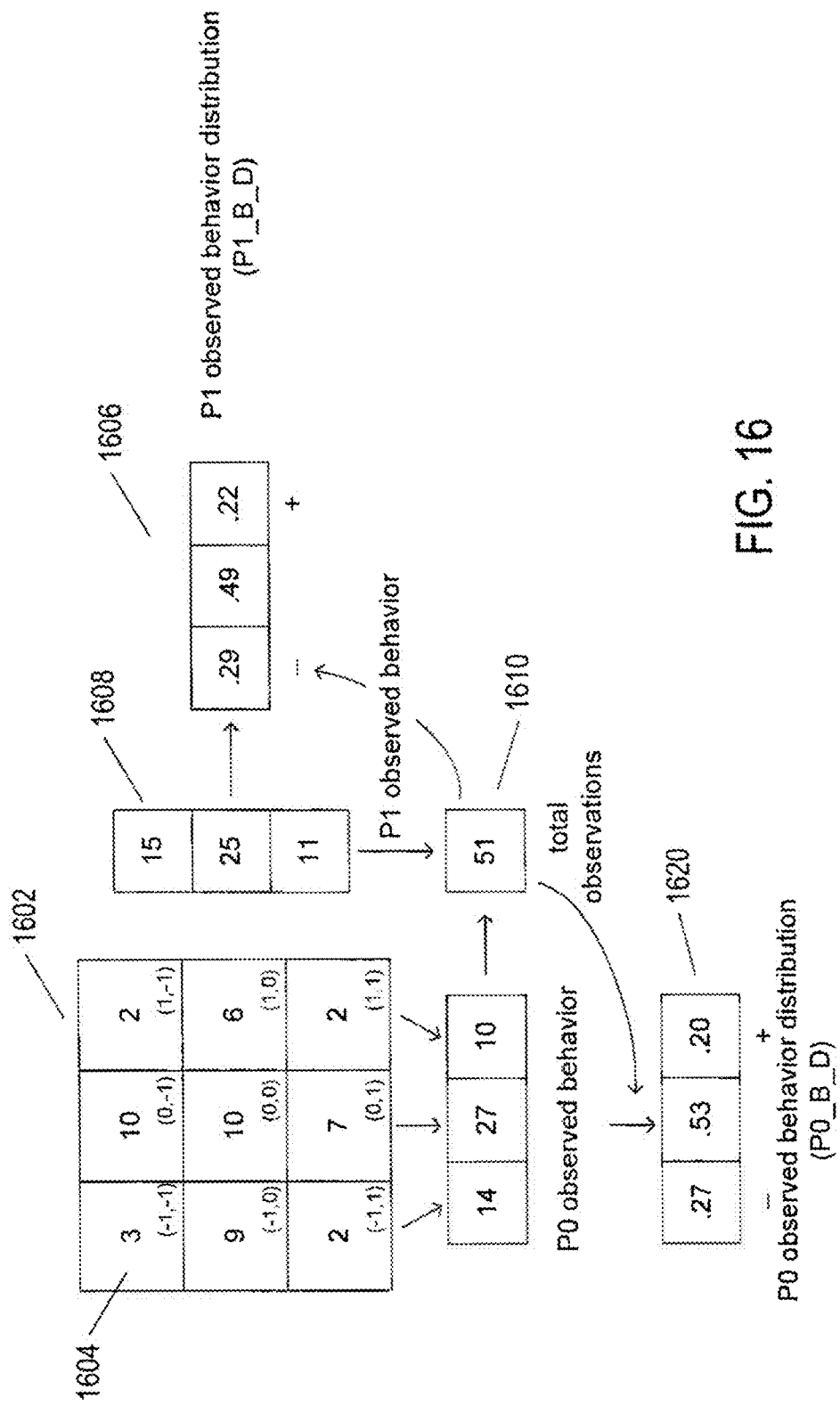
FIG. 16 illustrates generation of behavioral distributions for each of the participants.

FIG. 16 illustrates generation of behavioral distributions for each of the participants. Generation of the behavior distributions begins with a context matrix 1602. The columns and rows of this matrix have the same meaning as in the context-based preference matrices 1402 and 1404, discussed above. However, the values in the cells of this matrix represent the number of times that the corresponding context was observed in the collected data. For example, the value 3 in cell 1604 of the context matrix indicates that the context (−1, −1) was observed 3 times. Referring back to FIG. 12, this value is equal to the number of rating-dial values, or rows, in the block of rows 1224 corresponding to context (−1, −1). The behavior distribution for participant P1 1606 is obtained by summing the values in the rows of the context matrix and placing the row sums in a column vector 1608, adding the values in the column vector to produce a total number of observations 1610, transposing the column vector to a row vector and dividing each value in the row vector by the total number of observations to produce the behavior distribution 1606, referred to as P1_B_D in the following discussion. The behavior distribution for participant P0 1620 is similarly generated, as shown in FIG. 16, by summing the values in the columns of the context matrix 1602 and then dividing the sums by the total number of observations. The behavior distribution for participant P0 is referred to as P0_B_D in the following discussion.

FIG. 17 illustrates the process by which a trust metric is generated from preference and behavior distributions. A trust metric provides a quantitative measure of how well the objectively determined behavioral or emotional states exhibited by a first participant correspond to the preferences of the other participant contained in the preference distribution for the other participant. The trust metric thus provides a quantitative measure of how well a participant's exhibited behavioral or emotional states correspond to the other participant's preferences for the participant's behavioral or emotional states. The trust metric is not a measure of the frequency at which a participant exhibits positive behavioral or emotional states or the frequency at which a participant self-reports positive emotional responses. For example, according to the preference distributions 1514 and 1520 shown in FIG. 15, participant P0 appears to prefer negative and neutral behavioral or emotional states in participant P1. This being the case, the trust metric is a measure of how well the exhibited behavioral or emotional states of participant P1 correspond to the preferences of participant P0 encoded in the P0_P_D. When the behavioral or emotional states exhibited by participant P1 tend more towards the negative and neutral states the exhibited behavioral or emotional states of participant P1 tend to better match the preferences of participant P0. However, when the behavioral or emotional states exhibited by participant P1 become overly negative and/or neutral, the exhibited behavioral or emotional states of participant P1 would less well match the preferences of participant P0. The degree to which the behavioral or emotional states exhibited by a first participant match the preferences of a second participant corresponds to the degree of trust held by the second participant for the first participant. The trust metric can also be thought of as the degree to which the participant with which the trust metric is associated meets the other participant's expectations. Alternatively, a trust metric associated with a second participant is related to the degree to which a first participant perceives that the second participant acts in the first participant's interests.

As shown in FIG. 17, a divergence $D_x$ between the objectively determined behavioral and emotional states exhibited by participant x and the preferences by the other participant can be computed as:

$$D_x(P\_D_{\neg x}, B\_D_x) = \frac{1}{2}\left[\left(\sum_i P\_D_{\neg x}[i]\log_2\left(\frac{P\_D_{\neg x}[i]}{B\_D_x[i]}\right)\right) + \left(\sum_i B\_D_x\log_2\left(\frac{B\_D_x[i]}{P\_D_{\neg x}[i]}\right)\right)\right],$$

where $x \in \{0, 1\}$,
$\neg 0 = 1$,
$\neg 1 = 0$,
P_D is a preference distribution, and
B_D is a behavior distribution.

Because $$\log_2\left(\frac{x}{x}\right) = 0,$$

when the preference distribution $P\_D_{\neg x}$ is equal to the behavior distribution $B\_D_x$, the computed divergence $D_x$ is 0. The value of the divergence $D_x$ increases as the values of the two distributions diverge further from one another. Examples are provided below.

The trust metric associated with a participant x, which is the trust for that participant exhibited by the other participant ¬x, is calculated as:

$$TM_x = \max(1 - D_x, 0).$$

The maximum value for the trust metric is 1.0 and the minimum value for the trust metric is 0. The greater the value of the trust metric, the greater the trust held by participant ¬x for participant x. There are many additional ways to compute a value for the divergence between two distributions, including the Jensen-Shannon divergence, and any of those additional ways to compute a value for the divergence between two distributions can be used in order to compute a trust metric, provided that the same type of computed divergence is used for all trust metrics that are compared to one another.

FIGS. 18A-B illustrate trust metrics calculated for various example distributions. A first trust-metric calculation 1802, for participant P0 of the example discussed above with reference to FIGS. 10-16, shown at the top of FIG. 18A. A second trust-metric calculation 1804 is shown next, in FIG. 18A. In the example discussed above with reference to FIGS. 10-16, each participant has a significant level of trust for the other participant, but it is clear that participant P0 has greater trust for participant P1 than the participant P1 has for participant P0 based on the computed trust metrics $TM_1 = 0.942$ and $TM_0 = 0.915$. A third trust-metric calculation 1806 produces a very low trust-metric value computed for extremely divergent distributions while a fourth trust-metric calculation 1808 produces a very high trust-metric value for two very similar distributions. Example trust-metric computations shown in FIG. 18B produce intermediate-valued trust metrics for additional example distributions.

FIGS. 19A-F illustrate a process for computing trust metrics for two parties of a relationship. The labels and identifiers used in the example discussed above with reference to FIGS. 10-16 are used, for clarity, in the control-flow diagrams provided in FIGS. 19A and 19D-F. However, trust-metric computation is a generally applicable to data generated by many other types of relationship-evaluation and relationship-management systems.

Figure 19A:
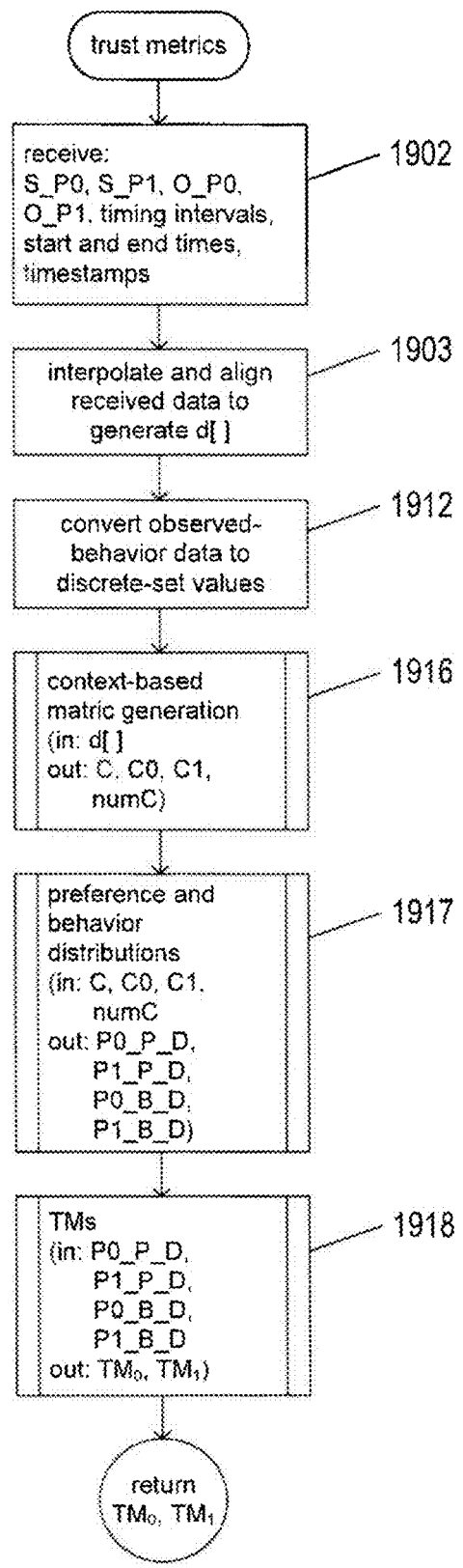
FIGS. 19A-F illustrate a process for computing trust metrics for two parties of a relationship.

FIG. 19A shows a control-flow diagram for a routine "trust metrics," which computes trust metrics for two parties to a relationship. In step 1902, the individual data sets S_P0, S_P1, O_P0, and OP_1, examples of which are discussed above with reference to FIGS. 10-12, are received along with additional information about the timing intervals, starting and ending times for the data collection, and, in certain cases, timestamps associated with one or more data points. As discussed above, the number of data points, time intervals between collection of adjacent data points, and other such parameters may vary depending on the nature of the relationship-analysis environment and data-collection procedures employed by the relationship-evaluation and relationship-management system. The individual data sets S_P0 and S_P1 contain subjective data with regard to the emotional states of the participants and the individual data sets O_P0 and O_P1 contain objective information about the behavioral or emotional states of the two participants. In different types of data-collection scenarios, the ranges of the numeric values included in the data sets may vary down the data-collection procedures may vary. In other cases, the collected data may be vector-valued data rather than scaler-value data.

Figure 19B:
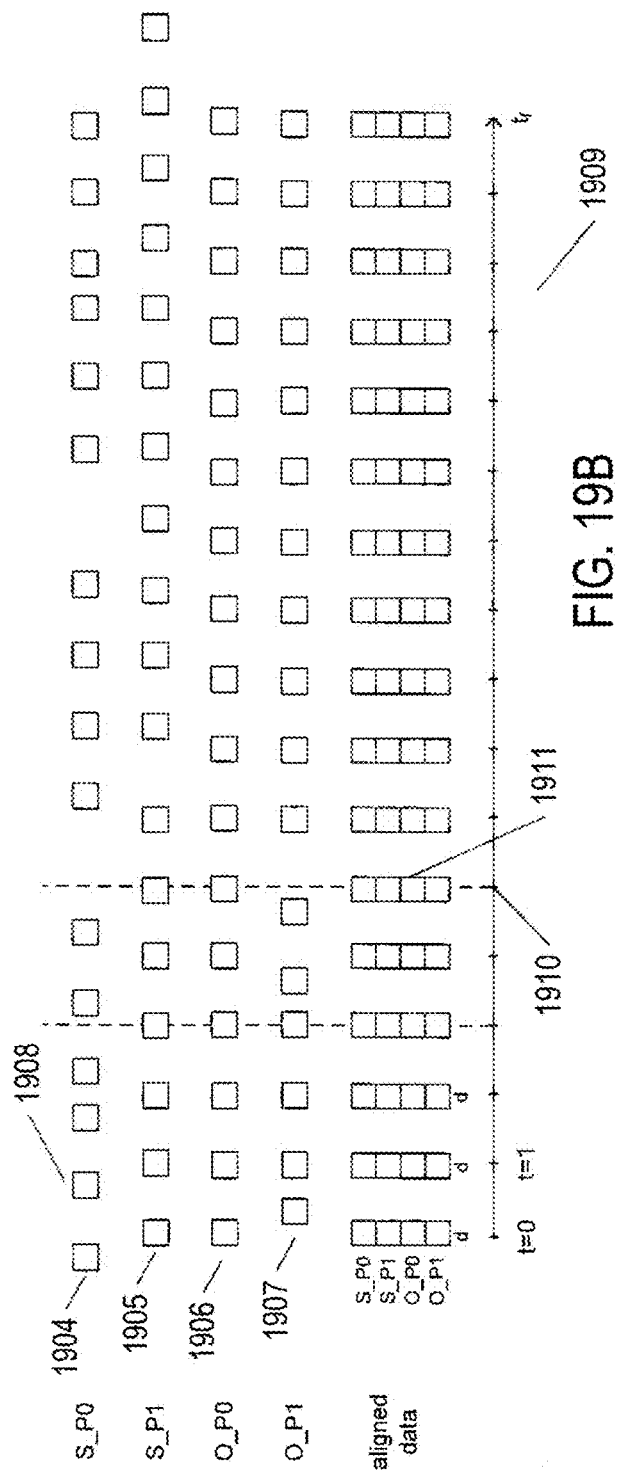

Next, in step 1903, the routine "trust metrics" interpolates and aligns the individual data sets with respect to time, as needed, in order to generate an observation data set. This process is illustrated in FIG. 19B. In FIG. 19 B, the initially received individual data sets are shown in the first four horizontal roles 1904-1907. Individual data points are represented by small squares, such as individual data point 1908 in individual data set S_P0. The positions of the individual data points in the horizontal direction represent time points with respect to a time axis 1909. In many cases, individual data points within the individual data sets are not well aligned with those of the other individual data sets. For example, at the point in time 1910, there is no corresponding data points for the S_P0 and O_P1 individual data sets. By various interpolation, estimation, and alignment procedures, reasonable data values for the missing data points can be generated in order to produce a vector-valued data point 1911 containing four data values for the four individual data sets at time point 1910. The observation data set thus contains data points for each of the individual data sets for each time point. In many cases, the collected data sets are complete and well aligned with respect to time, in which case step 1903 in FIG. 19A is not necessary. In other cases, the trust metrics can be computed from incomplete data without significant loss in accuracy, by, for example, omitting consideration of time points lacking data points for each of the individual component data sets, in which case step 1903 in FIG. 19A is also not necessary. The data values in the observation data set may be referred to as the data values of individual data sets or as elements of a vector-valued observation data set comprising the individual data sets.

Figure 19C:
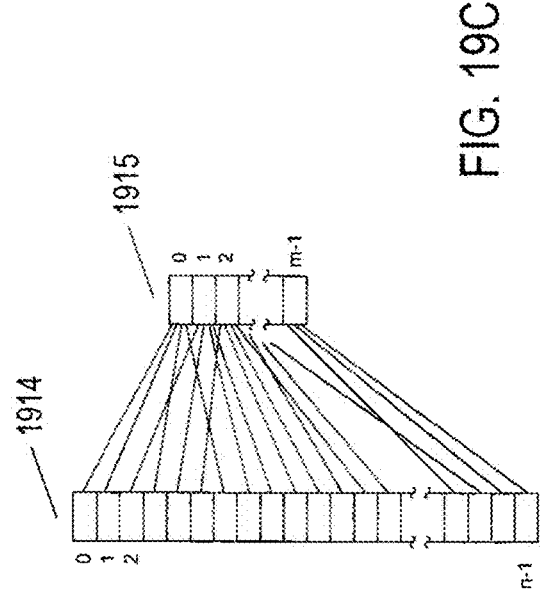

Next, in step 1912 of FIG. 19A, the objective-behavior data-set data values may be converted to corresponding data values selected from a discrete set. This process is illustrated in FIG. 19C. The originally collected objective-behavior data may include data values selected from a large number n of possible behavioral-encoding values, represented by column 1914 in FIG. 19C. Each of these possible data values may be mapped to one of a smaller set of discrete values, represented by a second column 1915 in FIG. 19C. In the example of FIGS. 10-16, the initially collected objective-behavior data values are selected from 20 possible behavioral-encoding values. These are mapped to the above-discussed negative, neutral, and positive behavioral or emotional states. In alternative implementations, such mappings may also be carried out on the self-reported subjective data sets. Many other types of initial processing steps may be employed, in alternative implementations, to generate a desired form of observation data in the observation data set produced in steps 1902, 1903, and 1912.

In step 1916, the context-based preference matrices and context matrix, generation of which are discussed above with reference to FIGS. 12-14 and 16, are generated from the observation data set. The observation data set may be an aggregation of individual data sets, an aggregation of individual data sets that have been aligned and completed, an aggregation of individual data sets, the data values of one or more of which have been mapped to discrete sets of data values, or an aggregation of individual data sets that have been aligned and completed and the data values of one or more of which have been mapped to discrete sets of data values In step 1917, the preference and behavior distributions are generated, as discussed above with reference to FIGS. 15 and 16. Finally, in step 1918, the two trust metrics $TM_0$ and $TM_1$ are generated, as discussed above with reference to FIG. 17.

Figure 19D:
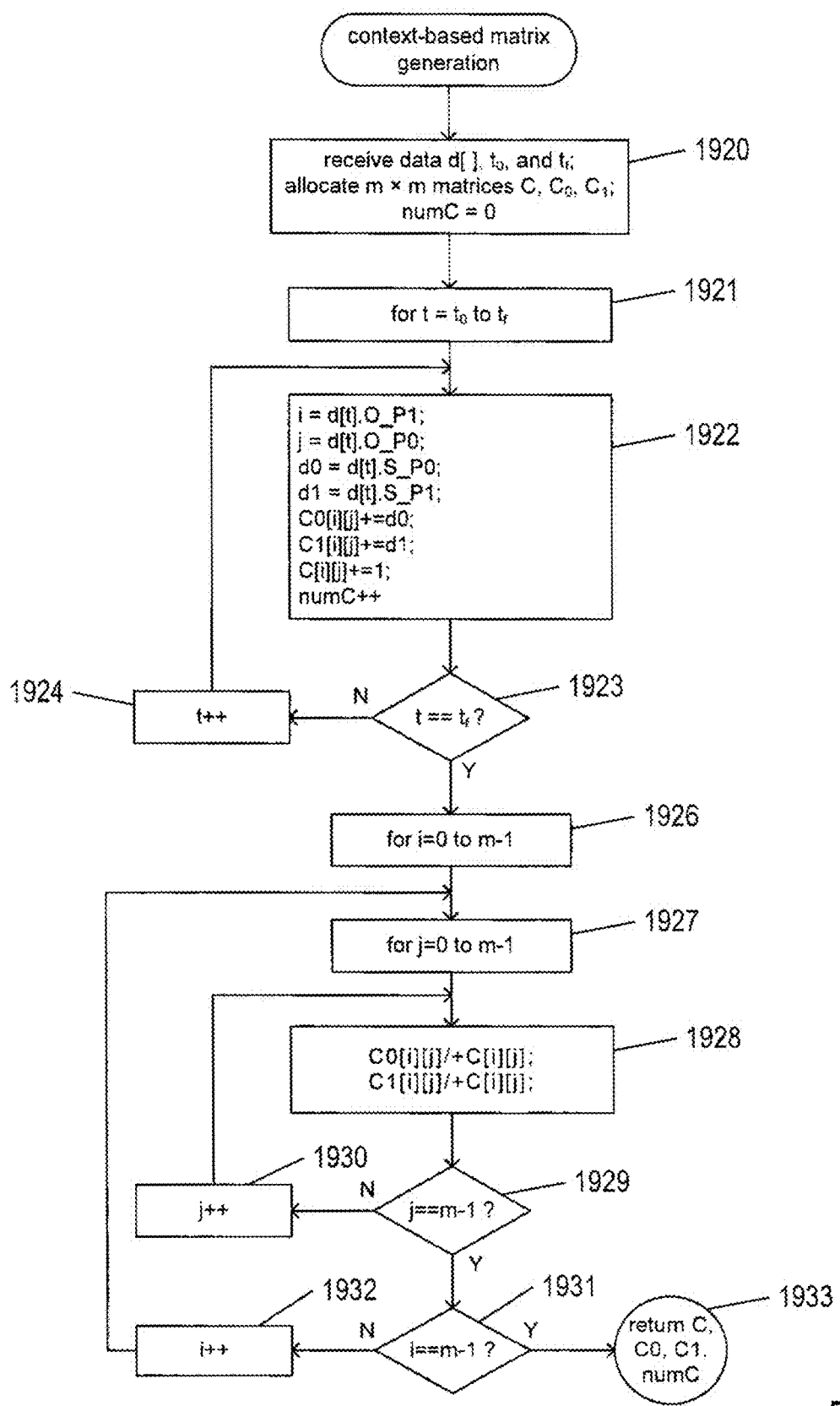

FIG. 19D provides a control-flow diagram for the routine "context-based matrix generation," called in step 1916 of FIG. 19A. In step 1920, the routine "context-based matrix generation" receives the observation data set d[ ] and the beginning and ending time points $t_0$ and $t_j$. Also in step 1920, the routine "context-based matrix generation" allocates three m×m matrices C, C0, and C1 corresponding to the context matrix and the two context-based preference matrices, where m is the number of different possible objective-behavior data values, and sets a local variable numC to 0. In the for-loop of steps 1921-1924, each data point in the observation data set is considered. For each data point, in step 1922, a pair of indices i and j are set to the objective-behavior values in individual data sets O_P0 and O_P1, which together comprise the context for the data point and which individually constitute indices for the cell for the context in the three context-based matrices C, C0, and C1. Then, the values of the cells of the three matrices corresponding to the context (i,j) are updated and the local variable ntC is incremented. In the doubly nested for-loop of steps 1926-1932, the values in the two preference matrices are divided by the number of observations that contributed to these values. In step 1933, the three matrices and the value stored in numC are returned.

Figure 19E:
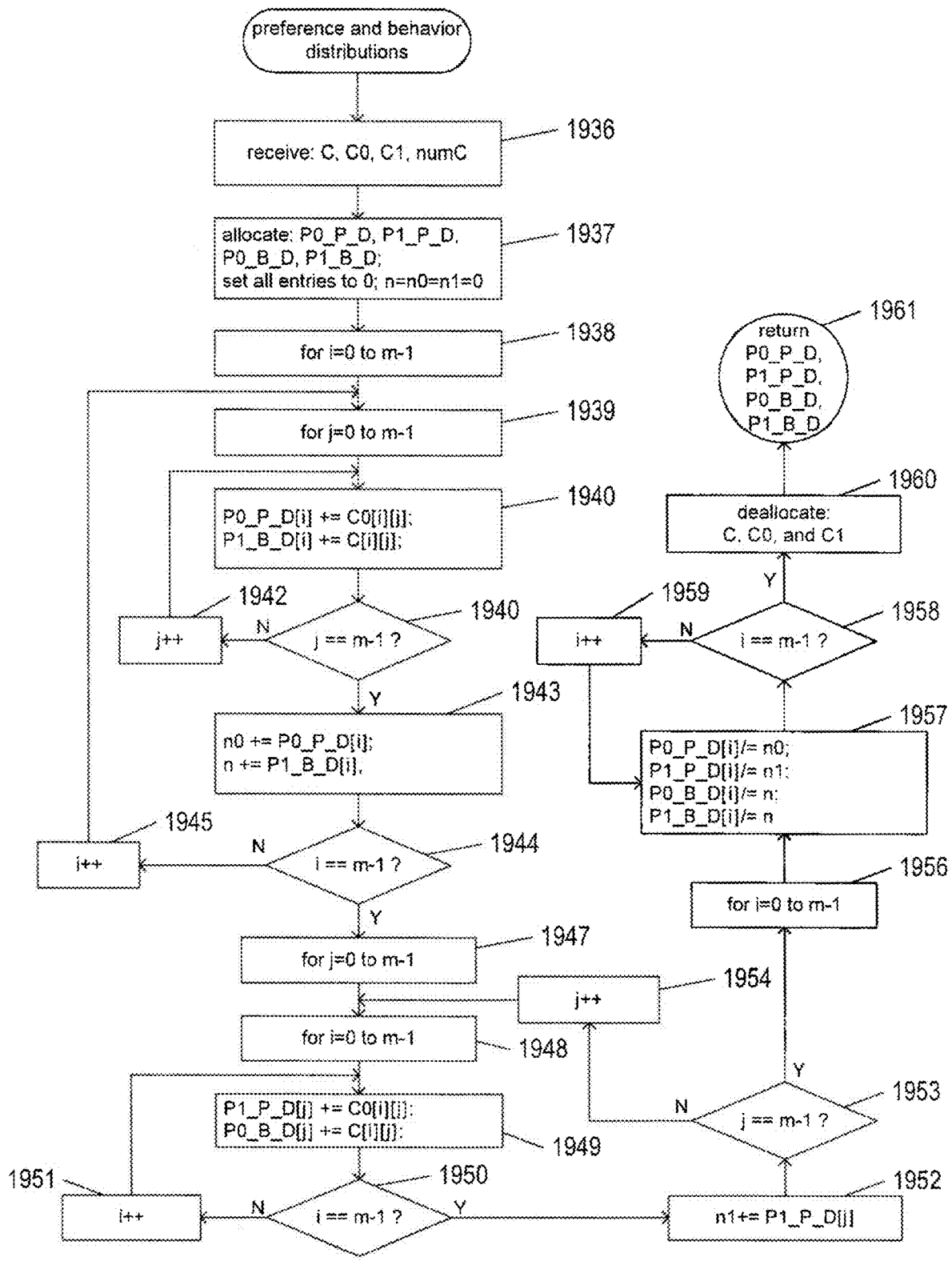

FIG. 19E provides a control-flow diagram for the routine "preference and behavior distributions" called in step 1917 of FIG. 19A. In step 1936, the routine "preference and behavior distributions" receives the output from the routine "context-based matrix generation." In step 1937, the routine "preference and behavior distributions" allocates row vectors for the four distributions P0_P_D, P1_P_D, P0_B_D, and P1_B_D, discussed above with reference to FIGS. 15 and 16, sets all entries in these distributions to 0, and sets three local variables n, n0, and n1 to 0. In the nested for-loops of steps 1938-1945, the sums of the rows in the C0 and C matrices are computed and stored in elements of the distributions P0_P_D and P1_B_D. In addition, the local variables n0 and n are updated to store the sum of the entries in the distributions P0_P_D and P1_B_D. In the nested for-loops of steps 1947-1954, the sums of the columns in the C1 and C matrices are computed and stored in elements of the distributions P1_P_D and P0_B_D. In addition, the local variable n1 is updated to store the sum of the entries in the distribution P1__D. Then, in the for-loop of steps 1956-1959, the elements of the distributions P0_P_D, P1_P_D, P0_B_D, and P1_B_D are divided by the value stored in the local variables n0, n1, n, and n, respectively, to generate the final preference and behavior distributions. In step 1960, the matrices C, C0, and C1 are deallocated. Finally, in step 1961, the four distributions P0_P_D, P1_P_D, P0_B_D, and P1_B_D are returned.

Figure 19F:
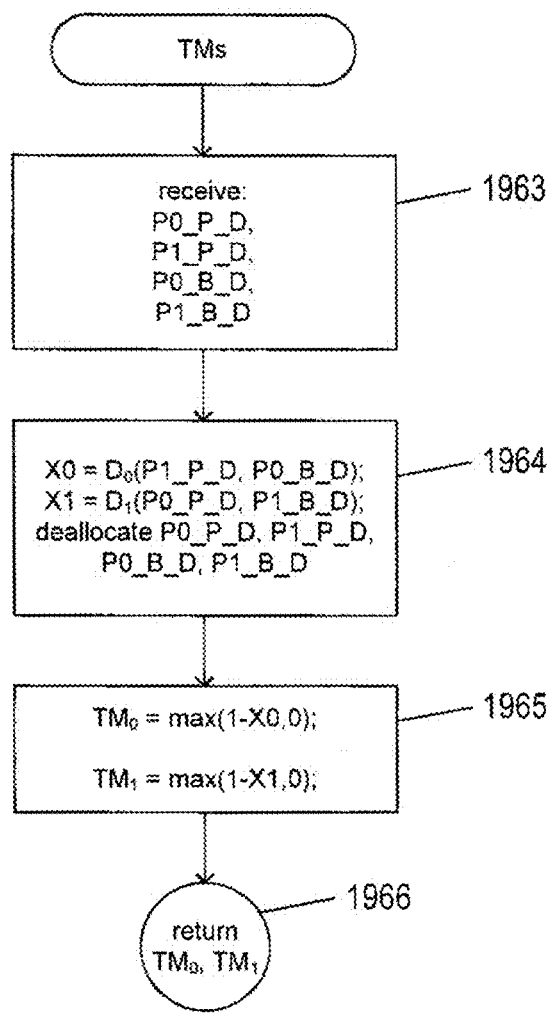

FIG. 19F provides a control-flow diagram for the routine "TMs" called in step 1918 of FIG. 19A. In step 1963, the routine "TMs" receives the output from the routine "preference and behavior distributions." In step 1964, the two divergences $D_0$ and $D_1$ are generated, as discussed above with reference to FIG. 17. Then, the four distributions P0_P_D, P1_P_D, P0_B_D, and P1_B_D are deallocated. Finally, in step 1965, the two trust metrics $TM_0$ and $TM_1$ are generated, as also discussed with reference to FIG. 17.

Figure 20:
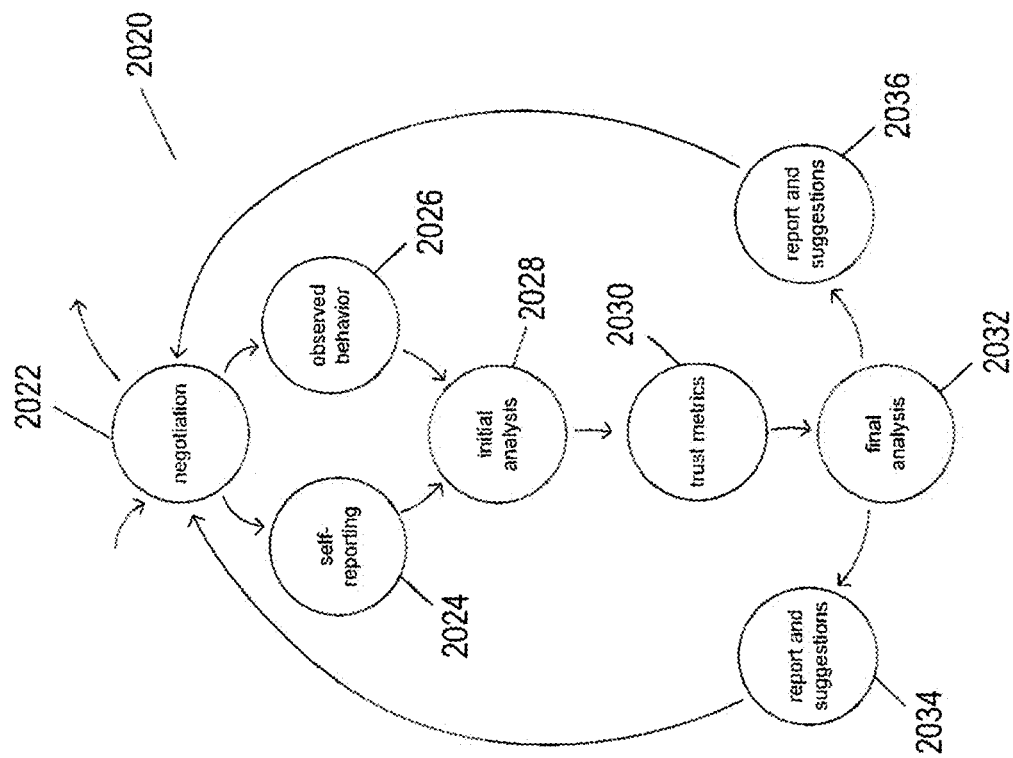
FIG. 20 illustrates the central position of trust-metric generation in various types of relationship-evaluation and relationship-management systems.
Figure 20:
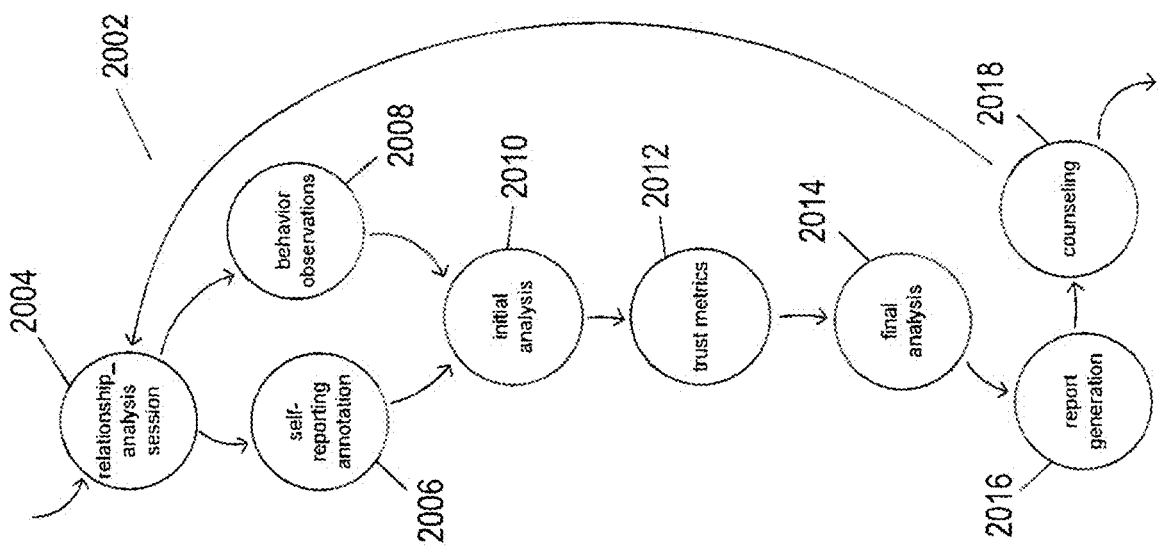

FIG. 20 illustrates the central position of trust-metric generation in various types of relationship-evaluation and relationship-management systems. A first state-transition diagram 2002 in FIG. 20 illustrates the central position of trust-metric generation in the semi-automated, distributed, interactive relationship-counseling system discussed above with reference to FIGS. 1A-4C. In a first phase, represented by state 2004, a relationship-analysis session is conducted. During a second phase, represented by states 2006 and 2008, subjective and objective data are collected. Then, beginning in state 2010, the collected data is analyzed. Following initial analysis, trust metrics are generated, in state 2012, as discussed above with reference to FIG. 17 and FIGS. 19A-F. Following generation of the trust metrics, a final analysis of the data, using the trust metrics, is carried out in state 2014. The results of the analysis are used for report generation, in state 2016, and for various types of counseling and therapy, in step 2018. The entire process may repeat numerous times. Generation of trust metrics, in step 2012, is fundamental to the analysis of the collected data in order to generate reports and to guide counseling.

A second state-transition diagram 2020 in FIG. 20 illustrates the central position of trust-metric generation in a negotiations-monitoring relationship-evaluation and relationship-management system. The negotiations are carried out, in state 2022, which may be exited and re-entered for each successive phase or stage of the negotiations. Following conclusion of a given phase, subjective and objective data is collected in states 2024 and 2026, respectively. Analysis of the collected data begins in state 2028, following which trust metrics are computed in state 2030. Following generation of trust metrics, a final comprehensive analysis is carried out in state 2032, leading to furnishing reports and suggestions to each negotiating party in states 2034 and 2036. Here again, a full analysis of the collected data is based on the trust metrics generated in step 2030 which, in turn, leads to generation of reports and suggestions that are then provided to the parties in the negotiation.

As indicated above, with reference to FIG. 20, generation of trust metrics is a fundamental process carried out in a variety of different higher-level computational processes that collect and analyze data in order to generate reports and initiate various actions carried out by the higher-level computational processes. In this respect, the trust metrics are a type of derived metadata that are input to, and control, a variety of downstream processes and tasks.

An R-programming-language implementation of a trust-metric-generation program is provided in Appendix A as an example of a working implementation of the trust-metric-generation portion of a relationship-analysis system. This implementation is not further described in the current document.

Although the present invention has been described in terms of particular embodiments, it is not intended that the invention be limited to these embodiments. Modifications within the spirit of the invention will be apparent to those skilled in the art. As discussed above, various different types of distribution-divergence metrics can be used to generate trust metrics. A variety of different implementation parameters may be varied to produce different implementations of the above-described trust-metric generation process, including use of different control structures, data structures, programming languages, operating systems, and underlying virtualization layers. Alternative implementations may produce trust metrics with different possible value ranges and with different detail the functional relationships to the observation data from which they are generated. Different types of observation data may be processed, in different implementations, to generate trust metrics.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

APPENDIX A

```
trust←function(spaff_fn, plot.flag=FALSE) {
  spaff_dir=file.path("C:\Data\\DataSPAFF")
  rating_dir=file.path("C:\\Data\\rating_dial")
  couple_id=substr(spaff_fn, 1, 8)
  files_rating=list.files(path=rating_dir)
  ##Read the data
  dat_spaff=readRDS(file.path(spaff_dir, spaff_fn))
  dat_rat=read.csv(file.path(rating_dir, files_rating[fn_rat_ind]), stringsAsFactors=F)
  ##Categorize spaff data
  dat_spaff=categorize_spaff(dat_spaff)
  dat_spaff[, "Time"]=as.numeric(seq.int(1, length.out=nrow(dat_spaff)))
  dat=cbind(dat_rat, dat_spaff)
  colnames(dat)=c("Time", "Spouse1_rat", "Spouse2_rat", "Time",
    "Spouse1_spaff", "Spouse2_spaff")
  if(plot.flag) {
    plot.series(dat.in=dat[, c("Spouse1_rat",
      "Spouse2_rat")], title=NULL, gr=c("line"))
    plot.series(dat.in=dat[, c("Spouse1_spaff",
      "Spouse2_spaff")], title=NULL, gr=c("point"))
  }
  ##Construct the context-based matrix
  trust_mtx_sp1=tapply(dat[,"Spouse1_rat"], list
    (dat$Spouse2_spaff, dat$Spouse1_spaff), mean)
  colnames(trust_mtx_sp1)←paste0(colnames(trust_mtx_sp1), "_sp1")
  rownames(trust_mtx_sp1)←paste0(rownames(trust_mtx_sp1), "_sp2")
  trust_mtx_sp1=cbind(trust_mtx_sp1, rowSums(trust_mtx_sp1))
  trust_mtx_sp1≈rbind(trust_mtx_sp1, colSums(trust_mtx_sp1))
  colnames(trust_mtx_sp1)[length(colnames(trust_mtx_sp1))]←"Totals_sp2"
  rownames(trust_mtx_sp1)[length(rownames(trust_mtx_sp1))]←"Totals_sp1"
  trust_mtx_sp2=tapply(dat[,"Spouse2_rat"], list
    (dat$Spouse2_spaff, dat$Spouse1_spaff), mean)
  colnames(trust_mtx_sp2)←paste0(colnames(trust_mtx_sp2), "_sp1")
  rownames(trust_mtx_sp2)←paste0(rownames(trust_mtx_sp2), "_sp2")
  trust_mtx_sp2=cbind(trust_mtx_sp2, rowSums(trust_mtx_sp2))
  trust_mtx_sp2≈rbind(trust_mtx_sp2, colSums(trust_mtx_sp2))
  colnames(trust_mtx_sp2)[length(colnames(trust_mtx_sp2))]←"Totals_sp2"
```

```
rownames(trust_mtx_sp2)[length(rownames(trust_
    mtx_.sp2))]←"Totals_sp1"
##Construct the context matrix
freq_mtx=table(dat[,                c("Spouse2_spaff",
    "Spouse1_spaff")])
freq_mtx=cbind(freq_mtx, rowSums(freq_mtx))
freq_mtx=rbind(freq_mtx, colSums(freq_mtx))
colnames(freq_mtx)[length(colnames(freq_mtx))]←"To-
    tals"
rownames(freq_mtx)[length(rownames(freq_mtx))]←
    "Totals"
##Proportions matrix
prop_mtx=freq_mtx/max(freq_mtx)
##Compute the trust metrics
##Compute the KL divergence
KL_div←function(p, q) {
    return(-sum(p*(log(q)-log(p))))
}
KL_div_sym←function(p, q) {
    return(0.5*(KL_div(p, q)+KL_div(q, p)))
}
##Strategies
P_sp2=head(prop_mtx[, "Totals"], -1)
P_sp1=head(prop_mtx["Totals",], -1)
##Optimal strategies
Q_sp2=apply(trust_mtx_sp1[-nrow(trust_mtx_sp1),-
    ncol(trust_mtx_sp1)], 1, max)
Q_sp2=Q_sp2/sum(Q_sp2)
Q_sp1=apply(trust_mtx_sp2[-nrow(trust_mtx_sp2),-
    ncol(trust_mtx_sp2)], 2, max)
Q_sp1=Q_sp1/sum(Q_sp1)
##KL divergence
D_sp2=KL_div_sym(P_sp2, Q_sp2)
D_sp1=KL_div_sym(P_sp1, Q_sp1)
KL_metric_sp2=max(1-KL_div_sym(P_sp2, Q_sp2), 0)
KL_metric_sp1=max(1-KL_div_sym(P_sp1, Q_sp1), 0)
out=list(Spouse1_Payoff_Matrix=trust_mtx_sp1
    , Spouse2_Payoff_Matrix=trust_mtx_sp2
    , Frequency_Matrix=freq_mtx
    , Proportions_Matrix=prop_mtx
    , Spouse1_Trust_Metric=trust_metric_sp1
    , Spouse2_Trust_Metric=trust_metric_sp2
    , Spouse1_KL_Div=D_sp1
    , Spouse2_KL_Div=D_sp2
    , Spouse1_KL_Trust_Metric=KL_metric_sp1
    , Spouse2_KL_Trust_Metric=KL_metric_sp2
)
out
}
categorize_spaff←function(dat.in) {
    ##Converts the raw spaff data into 3 categories: Neg,
        Neut, Pos
    sp.col.ind=grep("Spouse" colnames(dat.in))
    time.col.ind=grep("Time", colnames(dat.in))
    min.dat=min(dat.in[, sp.col.ind])
    max.dat=max(dat.in[, sp.col.ind])
    min.neut=5.5
    max.neut=6.5
    out=apply(dat.in[, sp.col.ind],2,
        cut, c(min.dat, min.neut, max.neut, max.dat), c("Neg",
            "Neut","Pos"))
    out=cbind(as.numeric(dat.in[, time.col.ind]), out)
    colnames(out)=c("Time", "Spouse.1", "Spouse.2")
    out[is.na(out)]←"Neut"
    out
}
```

The invention claimed is:

1. A relationship-analysis system employed by a relationship-evaluation-and-management system that collects data by monitoring an interaction or transaction of two parties, the relationship-analysis system comprising:
one or more processors,
one or more memories,
one or more mass-storage devices, and
computer instructions, stored in one or more of the one or more memories that, when executed by one or more of the one or more processors, control the relationship-analysis system to
receive, from the relationship-evaluation-and-management system, two sets of subjective data, one for each of the first party and the second party,
receive two sets of objective data, one for each of the first party and the second party,
generate an observation data set comprising the two sets of subjective data and two sets of objective data,
generate, from the observation data set, a preference distribution and a behavior distribution for each of the first and second parties,
generate and store, in one of the one or more memories, a trust metric for the first party from the behavior distribution generated for the first party and the preference distribution generated for the second party, the trust metric indicating a degree of trust held by the second party for the first party,
generate and store, in one of the one or more memories, a trust metric for the second party from the behavior distribution generated for the second party and the preference distribution generated for the first party, the trust metric indicating a degree of trust held by the first party for the second party, and
transmit the generated trust metrics to one more additional processes and/or subsystems within the relationship-evaluation-and-management system:
wherein the observation data set contains data points, each data point including a time point and a data value, each data value including a subjective data value for the first party, a subjective data value for the second party, and a context comprising an objective data value for the first party, and an objective data value for the second party;
wherein the preference distribution for the first party is a row vector that includes a cell for each objective data value, each cell containing a fraction computed as the sum of the subjective data values for the first party in the observation data set associated with time points for which the context in the observation data set includes an objective data value for the second party equal to the objective data value for the cell divided by the sum of the subjective data values for the first party in the observation data;
wherein the preference distribution or the second party is a row vector that includes a cell for each objective data value, each cell containing a fraction computed as the sum of the subjective data values for the second party in the observation data set associated with time points for which the context in the observation data set includes an objective data value for the first party equal to the objective data value for the cell divided by the sum of the subjective data values for the second party in the observation data;
wherein the behavior distribution for the first party is a row vector that includes a cell for each objective data value, each cell containing a fraction computed as the number of time points for which the objective data value for the second party in the observation data set is equal to the objective data value for the cell divided by the data points in the observation data; and wherein the behavior distribution for the second party is a row vector that includes a cell for each objective data value, each cell containing a fraction computed as the number of time points for which the objective data value for the first party in the observation data set is equal to the objective data value for the cell divided by the data points in the observation data.

2. A method performed by a relationship-analysis system employed by a relationship-evaluation-and-management system that collects data by monitoring an interaction or transaction of two parties, the relationship-analysis system having one or more processors, one or more memories, and one or more mass-storage devices, the method comprising:

receiving, from the relationship-evaluation-and-management system, two sets of subjective data, one for each of the first party and the second party, receiving two sets of objective data, one for each of the first party and the second generating an observation data set comprising the two sets of subjective data and two sets of objective data, generating, from the observation data set, a preference distribution and a behavior distribution for each of the first and second parties, generating and storing, in one of the one or more memories, a trust metric for the first party from the behavior distribution generated for the first party and the preference distribution generated for the second party, the trust metric indicating a degree of trust held by the second party for the first party, generating and storing, in one of the one or more memories, a trust metric for the second party from the behavior distribution generated for the second party and the preference distribution generated for the first party, the trust metric indicating a degree of trust held by the first party for the second party, and transmitting the generated trust metrics to one more additional processes and/or subsystems within the relationship-evaluation-and-management system;

wherein the observation data set contains data points, each data point including a time point and a data value, each data value including a subjective data value for the first party, a subjective data value for the second party, and a context comprising an objective data value for the first party, and an objective data value for the second party;

wherein the preference distribution for the first party is a row vector that includes a cell for each objective data value, each cell containing a fraction computed as the sum of the subjective data values for the first party in the observation data set associated with time points for which the context in the observation data set includes an objective data value for the second party equal to the objective data value for the cell divided by the sum of the subjective data values for the first party in the observation data;

wherein the preference distribution for the second party is a row vector that includes a cell for each objective data value, each cell containing a fraction computed as the sum of the subjective data values for the second party in the observation data set associated with time points for which the context in the observation data set includes an objective data value for the first party equal to the objective data value for the cell divided by the sum of the subjective data values for the second party in the observation data;

wherein the behavior distribution for the first party is a row vector that includes a cell for each objective data value, each cell containing a fraction computed as the number of time points for which the objective data value for the second party in the observation data set is equal to the objective data value for the cell divided by the data points in the observation data; and wherein the behavior distribution for the second party is a row vector that includes a cell for each objective data value, each cell containing a fraction computed as the number of time points for which the objective data value for the first party in the observation data set is equal to the objective data value for the cell divided by the data points in the observation data.

* * * * *